(12) United States Patent
Boone et al.

(10) Patent No.: US 9,295,576 B2
(45) Date of Patent: Mar. 29, 2016

(54) COMPUTERIZED ORTHOTIC PRESCRIPTION SYSTEM

(75) Inventors: David Alan Boone, Seattle, WA (US); Toshiki Kobayashi, Lynnwood, WA (US)

(73) Assignee: Orthocare Innovations LLC, Mountlake Terrace, WA (US)

( * ) Notice: Subject to any disclaimer, the term of this patent is extended or adjusted under 35 U.S.C. 154(b) by 1172 days.

(21) Appl. No.: 13/247,653

(22) Filed: Sep. 28, 2011

(65) Prior Publication Data

US 2012/0255160 A1    Oct. 11, 2012

Related U.S. Application Data

(60) Provisional application No. 61/387,321, filed on Sep. 28, 2010.

(51) Int. Cl.
*A61B 5/11* (2006.01)
*A61F 2/76* (2006.01)
(Continued)

(52) U.S. Cl.
CPC ............. *A61F 5/0111* (2013.01); *A61B 5/1038* (2013.01); *A61B 5/112* (2013.01); *A61B 5/6811* (2013.01); *A61B 5/6828* (2013.01); *A61B 5/6829* (2013.01); *A61F 5/0127* (2013.01); *G06Q 50/22* (2013.01); *A61F 2002/5049* (2013.01); *Y10T 29/49* (2015.01); *Y10T 29/49004* (2015.01); *Y10T 29/49764* (2015.01);
(Continued)

(58) Field of Classification Search
CPC ................ A61F 5/0111; A61F 5/0127; A61F 2002/5049; A61F 2002/5018; A61F 2002/503; A61F 2002/7635; A61F 2002/7645; A61F 2002/5033; A61B 5/6811; A61B 5/6828; A61B 5/112; A61B 5/1038; A61B 5/6829; G06Q 50/22; Y10T 29/49004; Y10T 29/49771; Y10T 29/49774; Y10T 29/49776; Y10T 29/49778; Y10T 29/49764
USPC ............... 29/407.01, 407.09, 407.08, 407.05, 29/595, 593; 600/587, 592, 595; 623/24, 623/38; 601/5; 606/1
See application file for complete search history.

(56) References Cited

U.S. PATENT DOCUMENTS 4,236,528 A * 12/1980 Stanec et al. .................. 600/554
4,738,269 A *  4/1988 Nashner ........................ 600/595
(Continued)

FOREIGN PATENT DOCUMENTS

WO   WO 03063730 A1 *  8/2003 ................ A61F 5/00
WO   WO 2008005865 A1 *  1/2008 ................ A61F 5/01

OTHER PUBLICATIONS

International Search Report and Written Opinion mailed Apr. 30, 2012, issued in corresponding International Application No. PCT/US2011/053734, filed Sep. 28, 2011, 6 pages.

*Primary Examiner* — David Bryant
*Assistant Examiner* — Bayan Salone
(74) *Attorney, Agent, or Firm* — Christensen O'Connor Johnson Kindness PLLC

(57) ABSTRACT

A method for tuning an orthosis for the correct stiffness and/or shank angle includes via one or more computers, receiving patient information including forces experienced by a joint of a patient wearing an orthosis, wherein the orthosis has a degree of stiffness and a shank angle, via one or more computers, comparing the patient information to model information, wherein the model information includes the forces of a correctly functioning joint, and changing the degree of stiffness and/or the shank angle of the orthosis.

17 Claims, 18 Drawing Sheets

(51) Int. Cl.
*A61F 2/50* (2006.01)
*A61B 5/00* (2006.01)
*A61B 5/103* (2006.01)
*A61F 5/01* (2006.01)
*G06Q 50/22* (2012.01)

(52) U.S. Cl.
CPC ...... *Y10T 29/49771* (2015.01); *Y10T 29/49773* (2015.01); *Y10T 29/49774* (2015.01); *Y10T 29/49776* (2015.01); *Y10T 29/49778* (2015.01)

(56) References Cited

U.S. PATENT DOCUMENTS

| | | | | |
|---|---|---|---|---|
| 5,038,795 | A * | 8/1991 | Roush et al. | 600/587 |
| 5,044,360 | A * | 9/1991 | Janke | 602/16 |
| 5,050,618 | A * | 9/1991 | Larsen | 600/587 |
| 5,121,742 | A * | 6/1992 | Engen | 602/16 |
| 5,297,540 | A * | 3/1994 | Kaiser et al. | 601/27 |
| 5,313,968 | A * | 5/1994 | Logan et al. | 600/595 |
| 5,328,444 | A * | 7/1994 | Whiteside | 602/16 |
| 5,687,467 | A * | 11/1997 | Bergmann et al. | 29/407.05 |
| 5,800,565 | A * | 9/1998 | Biedermann | 623/38 |
| 5,979,067 | A * | 11/1999 | Waters | 33/512 |
| 5,980,472 | A * | 11/1999 | Seyl | 600/587 |
| 6,006,412 | A * | 12/1999 | Bergmann et al. | 29/407.04 |
| 6,045,517 | A * | 4/2000 | Williams | 600/587 |
| 6,219,929 | B1 | 4/2001 | Tasker et al. | 33/515 |
| 6,254,559 | B1 * | 7/2001 | Tyrrell | 602/16 |
| 6,287,253 | B1 * | 9/2001 | Ortega et al. | 600/300 |
| 6,371,123 | B1 * | 4/2002 | Stark et al. | 128/898 |
| 6,409,684 | B1 | 6/2002 | Wilk | 600/586 |
| 6,589,190 | B2 * | 7/2003 | Kanderian et al. | 600/587 |
| 6,599,255 | B2 * | 7/2003 | Zhang | 600/587 |
| 6,792,801 | B2 * | 9/2004 | Hoggan et al. | 73/379.02 |
| 6,945,947 | B2 * | 9/2005 | Ingimundarson et al. | 602/27 |
| 7,010,869 | B1 * | 3/2006 | Ellis, III | 36/25 R |
| 7,077,818 | B2 * | 7/2006 | Ingimundarson et al. | 602/27 |
| 7,204,814 | B2 * | 4/2007 | Peles | 601/5 |
| 7,544,155 | B2 * | 6/2009 | Agrawal et al. | 482/69 |
| 7,563,234 | B2 * | 7/2009 | Cordo | 601/5 |
| 7,650,204 | B2 * | 1/2010 | Dariush | 700/245 |
| 7,793,429 | B2 * | 9/2010 | Ellis, III | 36/25 R |
| 7,886,618 | B2 * | 2/2011 | Macomber et al. | 73/862.044 |
| 7,922,774 | B2 * | 4/2011 | Macomber et al. | 623/27 |
| 7,985,193 | B2 * | 7/2011 | Thorsteinsson et al. | 602/16 |
| 8,075,501 | B2 * | 12/2011 | Miller et al. | 600/592 |
| 8,075,633 | B2 * | 12/2011 | Herr et al. | 623/47 |
| 8,197,425 | B2 * | 6/2012 | Kobayashi et al. | 600/595 |
| 8,215,186 | B2 * | 7/2012 | Macomber et al. | 73/862.044 |
| 8,261,468 | B2 * | 9/2012 | Ellis, III | 36/25 R |
| 8,475,397 | B2 * | 7/2013 | Chiu et al. | 602/28 |
| 8,500,668 | B2 * | 8/2013 | Siegler et al. | 602/23 |
| 8,636,627 | B2 * | 1/2014 | Zhang et al. | 482/52 |
| 8,678,979 | B2 * | 3/2014 | Stark et al. | 482/8 |
| 8,784,502 | B2 * | 7/2014 | Macomber et al. | 623/39 |
| 2002/0029784 | A1 * | 3/2002 | Stark et al. | 128/898 |
| 2002/0188238 | A1 * | 12/2002 | Townsend et al. | 602/26 |
| 2005/0043661 | A1 * | 2/2005 | Nashner | 602/26 |
| 2005/0059908 | A1 * | 3/2005 | Bogert | 601/5 |
| 2005/0070834 | A1 * | 3/2005 | Herr et al. | 602/28 |
| 2005/0288609 | A1 * | 12/2005 | Warner et al. | 600/592 |
| 2006/0195197 | A1 * | 8/2006 | Clausen et al. | 623/24 |
| 2006/0206214 | A1 * | 9/2006 | Clausen et al. | 623/24 |
| 2006/0241539 | A1 * | 10/2006 | Agrawal et al. | 602/23 |
| 2006/0270950 | A1 * | 11/2006 | Dariush | 601/5 |
| 2006/0276728 | A1 * | 12/2006 | Ashihara et al. | 601/5 |
| 2007/0271817 | A1 * | 11/2007 | Ellis, III | 36/28 |
| 2008/0139968 | A1 * | 6/2008 | Endo et al. | 600/595 |
| 2008/0140221 | A1 * | 6/2008 | Macomber et al. | 623/27 |
| 2009/0171469 | A1 * | 7/2009 | Thorsteinsson et al. | 623/26 |
| 2009/0183388 | A1 * | 7/2009 | Miller et al. | 36/43 |
| 2010/0145233 | A1 * | 6/2010 | Zhang et al. | 600/592 |
| 2011/0130684 | A1 * | 6/2011 | Macomber et al. | 600/587 |
| 2013/0197318 | A1 * | 8/2013 | Herr et al. | 600/301 |

* cited by examiner

COMPUTERIZED ORTHOTIC PRESCRIPTION SYSTEM

CROSS-REFERENCE TO RELATED APPLICATION

This application claims the benefit of U.S. Provisional Application No. 61/387,321, filed Sep. 28, 2010, which is fully incorporated herein expressly by reference.

BACKGROUND

An orthosis is any apparatus that may be used to correct or support parts of the body to improve function, reduce discomfort, or to provide increased mobility for a patient. Orthoses are available to address medical problems with parts of the lower body, including the hip, leg, knee, ankle, and foot.

A nonexhaustive list of orthoses includes, an ankle-foot orthosis (AFO), a knee-ankle-foot orthosis (KAFO), a hip-knee-ankle-foot orthosis (HKAFO), and a foot orthosis (FO).

A common feature among all the orthoses types is the ability to adjust, modify, or make a correction to ideally suit the orthosis to the patient for which it is intended. For example, many orthoses, especially orthoses for joints, can be made more or less stiff. Additionally, the shank angle may also be adjusted.

Referring to FIG. 1A, an AFO 100 is illustrated. An AFO helps to support the foot in relation to the ankle joint. One particular AFO is a molded piece of semirigid material, such as plastic or carbon fiber, having a sole portion 102 connected to a heel cup 104 and an Achilles portion 106 extending upwards along the Achilles tendon that terminates at or near the calf muscles. The Achilles portion 106, which extends upwards, can wrap around the lower leg, and may even extend anteriorly. The Achilles portion 106 may be secured to the lower leg, while the sole portion is secured to the foot. The amount of material that is used in the upwardly extending Achilles portion determines the stiffness and/or the shank angle of the AFO 100 with respect to ankle joint stiffness and foot dorsiflexion. The stiffness may be considered, in part, to be the degree to which the Achilles portion is resistance to flexing with respect to the foot sole. The shank angle may be considered the angle between the upright portion (Achilles portion) and the foot sole. An AFO may be prescribed to a patient with weakened plantar flexor muscles. When these muscles are working properly, they store energy much like a spring. This energy is released during walking in the propulsion or push-off phase. Thus, a person with functioning muscles can be more energy efficient during walking. However, a patient with weakened muscles has a reduced ability to store or release energy in the ankle. Thus, an AFO is prescribed to replace the function of the weakened muscles. An AFO must behave like a spring; thus, it must be flexible and have memory so that it returns to its original configuration. Like a spring, an AFO has a certain degree of stiffness and a certain shank angle. Many AFOs can be tuned to change the stiffness and/or shank angle.

As shown in FIG. 1B, an AFO 108 may begin as a "universal" AFO 108, which includes extensive wrap around sides. Depending on the condition of the patient, the universal AFO 108 can be modified by cutting along the dotted trimming lines 110 shown in FIG. 1B. By cutting greater amounts of material, the orthosis stiffness is reduced.

FIG. 1C shows an alternative AFO 112 including a foot sole 116 with heel cup and an Achilles portion 114, which attaches to the distal part of the leg. Unlike the AFO illustrated in FIGS. 1A and 1B, the AFO illustrated in FIG. 1C comprises two molded pieces of plastic which are attached to each other at a pivoting hinge 118. Thus, stiffness and shank angle is adjusted in the articulated AFO by manipulating a property of the joint 118 between the sole 116 and the Achilles portion 114.

In order to prescribe an orthosis with the proper stiffness and/or shank angle, an orthotist may rely on experience, clinical examination, or a patient interview. However, the orthotist does not have many other tools at his disposal for prescribing the suitable stiffness and/or shank angle of an orthosis.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Disclosed are methods for tuning an orthosis. In some embodiments, the orthosis is tuned for correct stiffness. In some embodiments, the orthosis is tuned for correct shank angle. In some embodiments, the orthosis is tuned for both or either the correct stiffness and shank angle.

In one embodiment, a method for tuning an orthosis to achieve a correct stiffness and/or shank angle is disclosed. The method includes, via one or more computers, receiving patient information including forces experienced by a joint of a patient wearing an orthosis, wherein the orthosis has a degree of stiffness and/or shank angle. The method includes, via one or more computers, comparing the patient information to model information, wherein the model information includes the forces of a correctly functioning joint. The method includes changing the degree of stiffness and/or shank angle of the orthosis.

In one embodiment, a method for tuning an orthosis for correct stiffness and/or shank angle is disclosed. The method includes placing an insole sensor in a shoe of a patient wearing an orthosis over a joint, wherein the insole sensor includes sensors forward and to the rear of the ankle joint. The method includes allowing the patient to walk with the sensor. The method includes collecting patient information from the insole sensor, including forces sensed by the forward and rear sensors. The method includes comparing the patient information to model information, wherein the model information includes the forces of a correctly functioning joint. The method includes changing a degree of stiffness and/or shank angle of the orthosis.

The methods may further include, via the one or more computers, providing a deviation between the patient information and the model information.

The methods may further include, via the one or more computers, providing a recommendation on whether to increase or decrease stiffness and/or shank angle of the orthosis.

The methods may further include sending a recommendation over a network, such as the Internet.

The methods may further include sending patient information from a local computer over a network to a remote server, and sending recommendations from the remote server to the local computer.

The methods may be used to tune an orthosis configured to be worn over body joints, including, but not limited to ankles, knees, and hips.

The methods may further include, via the one or more computers, receiving patient physical information that describes a distance from the joint to a reference point. The joint may be an ankle, and the reference point is located at the posterior of the heel along a horizontal line from the ankle.

The methods may further include trimming a portion of the orthosis to decrease stiffness.

The methods may further include increasing or decreasing the friction of a mechanical pivot linking two components of an orthosis.

The methods may further include increasing or decreasing the shank angle of the orthosis.

The methods may include compiling patient information from information gathered during walking as a patient's foot contacts the ground.

The methods may include correcting the model information for the weight of the patient.

The methods may include compiling the model information from samples of correctly functioning joints.

The methods may include measuring the forces and moments causing the joint to rotate.

The methods may further include displaying a graph of the patient information.

The methods may further include displaying a graph of the model information.

The methods may further include, after making a change to the orthosis with respect to stiffness, shank angle, or both, allowing the patient to walk with the changed orthosis, collecting patient information from the insole sensor, including forces sensed by the forward and rear sensors, comparing patient information to model information, wherein the model information includes the forces of a correctly functioning joint.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Disclosed herein are methods for prescribing a stiffness and/or shank angle of an orthosis. The shank angle may be described as the unloaded neutral dorsiflexion angle of the orthosis. The shank angle is closely related to stiffness and creates the "perceived stiffness," but is separate from the mechanical stiffness itself since the amputee patient can achieve the shank angle without resistance. Clinically, this is an important distinction to maximize efficiency while maintaining comfort. In one embodiment, the method includes measuring the moments experienced by an ankle joint. Particularly, moments that are parallel with the sagittal plane (anterior/posterior plane) are measured. While an ankle joint is used to illustrate embodiments of the invention, the methods may be used for prescribing the correct stiffness of other joints, including the knee, or hip. The methods may be used to assist orthotists in tuning the correct stiffness and/or shank angle of orthoses, including, but not limited to, an AFO.

Figure 2:
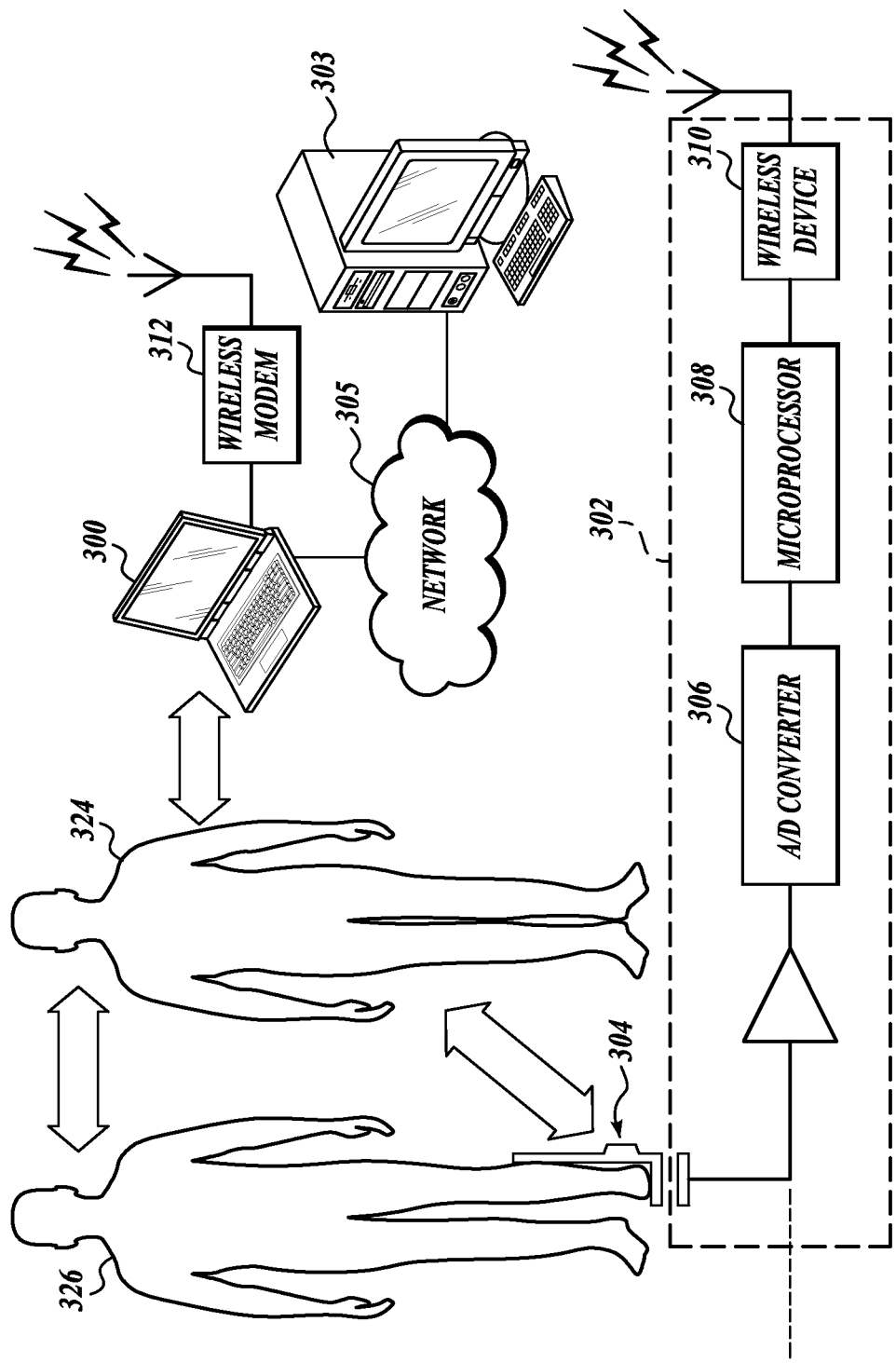
FIG. 2 is a schematic illustration showing the computerized orthotic prescription system.

Referring to FIG. 2, a schematic illustration is shown of a computerized orthotic prescription system. The system may be used by an orthotist (user) 324 when working with a patient 326 to prescribe a suitable orthosis, such as an AFO. While an AFO is used to illustrate one embodiment of the invention, the invention is not to be construed as being limited to one particular orthosis. Furthermore, orthoses include prostheses, such as a lower limb prosthesis including a prosthetic foot, and socket.

The system comprises an insole sensor 302, preferably with wireless capability and a computer 300, able to receive information from the sensor 302. The sensor may include, at least, an analog-to-digital converter 306, a microprocessor 308, and a wireless device 310 to communicate to the computer 300. The computer 300 is operated by the orthotist 324, who then interacts with the patient 326. The computer 300 is programmed with applications. The applications running on the computer 300 receive inputs, such as physical measurements pertaining to the patient, receive patient information via the sensor 302 as the patient walks with an orthosis 304, receive model information pertaining to a correct orthosis stiffness and/or shank angle, and use the information to make suggestions to make corrections in the orthosis stiffness and/or shank angle. As used herein, patient information includes the forces or moments sensed by the sensor 302 as a patient walks.

In one embodiment of the invention, a method uses the correlation of the forces (moments) experienced by the ankle joint to determine the correct stiffness and/or shank angle of an orthosis. The method compares the moments sensed during walking to a model. From the comparison between the patient information to the model information, the method makes suggestions whether the orthosis is too stiff or not stiff enough and regarding whether the shank angle is correct. The model is derived from correlations between ankle moments and orthosis stiffness and shank angles determined in advance. The model of optimal stiffness and/or shank angle may be created, for example, by acquiring a training set of data compiled from numerous subjects considered to be "good" samples having the correct ankle joint stiffness and/or shank angle. The training data set used to create the model can further be classified by weight, stature, and other physical attributes, so that the model can be suited to the particular patient.

Figure 3:
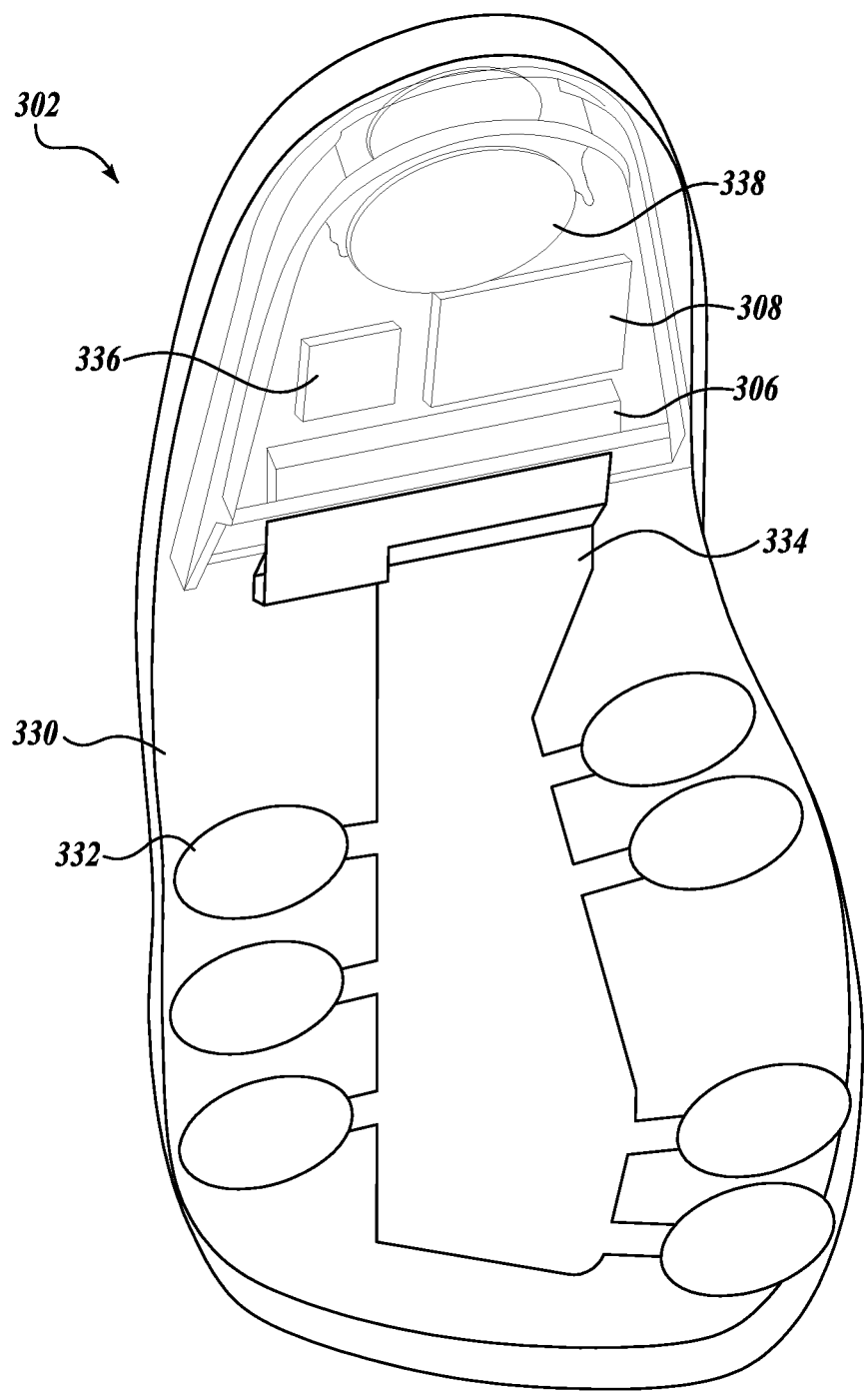
FIG. 3 is a diagrammatical illustration of an insole sensor for the computerized orthotic prescription system.

Referring to FIG. 3, a diagrammatical illustration of an insole sensor 302 is illustrated. One embodiment of the insole sensor may include a flexible silicone gel body 330 for encapsulating the components of the sensor 302. The insole sensor shape generally resembles the foot and has a narrow heel portion, a curved arch section, and a broader width at the toe section. The insole sensor 302 may be worn by a patient inside of a shoe, together with the orthosis. The insole sensor 302 includes one or more pressure sensors 332, 338 encapsulated within the silicone gel insole 330. A plurality of pressure sensors may be placed on the medial and lateral sides of the insole. A plurality of pressure sensors 332 may be placed in a forward section of the insole sensor, such that the pressure sensors are forward of the ankle joint. Additionally, pressure sensors 338 may be placed on the heel portion of the insole, such that the pressure sensors are behind the ankle joint. In one embodiment, three sensors are placed on a side, and two pairs of two sensors are placed on the opposite side. In one embodiment, the three sensors are placed on the lateral side of the insole, and the two pairs of two sensors are placed on the medial side of the sensor. Sensors may be placed forward of the ankle, as shown, and to the rear of the ankle, such as on the heel portion. This allows the measurement of forces from the moment of contact of the heel throughout the stand phase until toe-off. As is conventional, "lateral" refers to a direction facing away from the center of the body, and "medial" refers to a direction facing in a direction toward the center of the body. The pressure sensors may include materials that deflect in some manner and such deflection can affect the materials' electrical resistance, and thus, cause a change in voltage. Such sensors are well-known. The pressure sensors are connected via flexible conductors 334 to other electronic modules in the sensor 302. The sensor 302 may include an A/D converter 306, microprocessor 308, storage device in the form of memory 336. The electronics may provide for filtering of the signal, amplification, and conversion to digital format. Such electronics modules are well-known. Additionally, in one embodiment, the insole sensor 302 may include any wireless technology capable of transmitting signals to the computer 300. The wireless communications protocol may be any short-range radio frequency protocol, such as Bluetooth. The insole sensor 302 may include a power supply, such as a battery to power the sensors 332.

The sensor 302 may include various electronic components for signal conditioning, temperature compensation, analog-to-digital conversion, digital-to-analog conversion and a serial communication bus. Additionally, sensor calibration data are stored in an onboard memory. The memory 336 may also serve to record data over an extended period of time, such as when a patient wears the orthosis in the normal course of a day. Patient records and other patient treatment data may also be stored in the onboard memory. The memory 336 can be any volatile or non-volatile memory, such as, but not limited to, PROM, EEPROM, Flash, DRAM, eDRAM, and PROM to name a few representative examples. The memory 336 holds sensor calibration data, and, alternatively, the memory 336 may hold patient information data that is recorded over an extended period of time, such as when a patient wears the orthosis in the normal course of a day.

The system includes one or more computers 300. While shown as a single stand alone computer, persons of skill in the art will appreciate that computer 300 may be more than one computer, distributed locally or remotely to one another. The computer stores algorithms for performing comparisons of the information collected from the patient to model information. The applications running the one or more computers may be described in the context of computer-executable instructions, such as program modules being executed by the host computer. Generally described, program modules include routines, programs, applications, objects, components, data structures, and the like that perform tasks or implement particular abstract data types. The following description provides a general overview of a computer with which the method for prescribing an orthosis may be implemented. The applications can be stored on the computer 300 or in a remote server 303 to which the computer 300 is communicatively linked to, such as through the Internet 305. In one embodiment, for example, one computer may be local, for example, at an orthotist's office. The local computer 300 may send patient information over a network, such as the Internet 305, to a remote server 303. The remote server 303 processes the information, and the remote server 303 returns information, such as a recommendation to the local computer 300, which then displays the information to the orthotist. The provider of the remote server may charge a fee for providing a prescription service. Furthermore, the remote server may also store all of the patient information to avoid storage on the local computer. Any communication over the Internet or other network may be encrypted for security.

The illustrative examples provided herein are not intended to be exhaustive or to limit the invention to the precise forms disclosed. Similarly, any steps described herein may be interchangeable with other steps or a combination of steps or, be arranged in a different sequence in order to achieve the same result.

Figure 4:
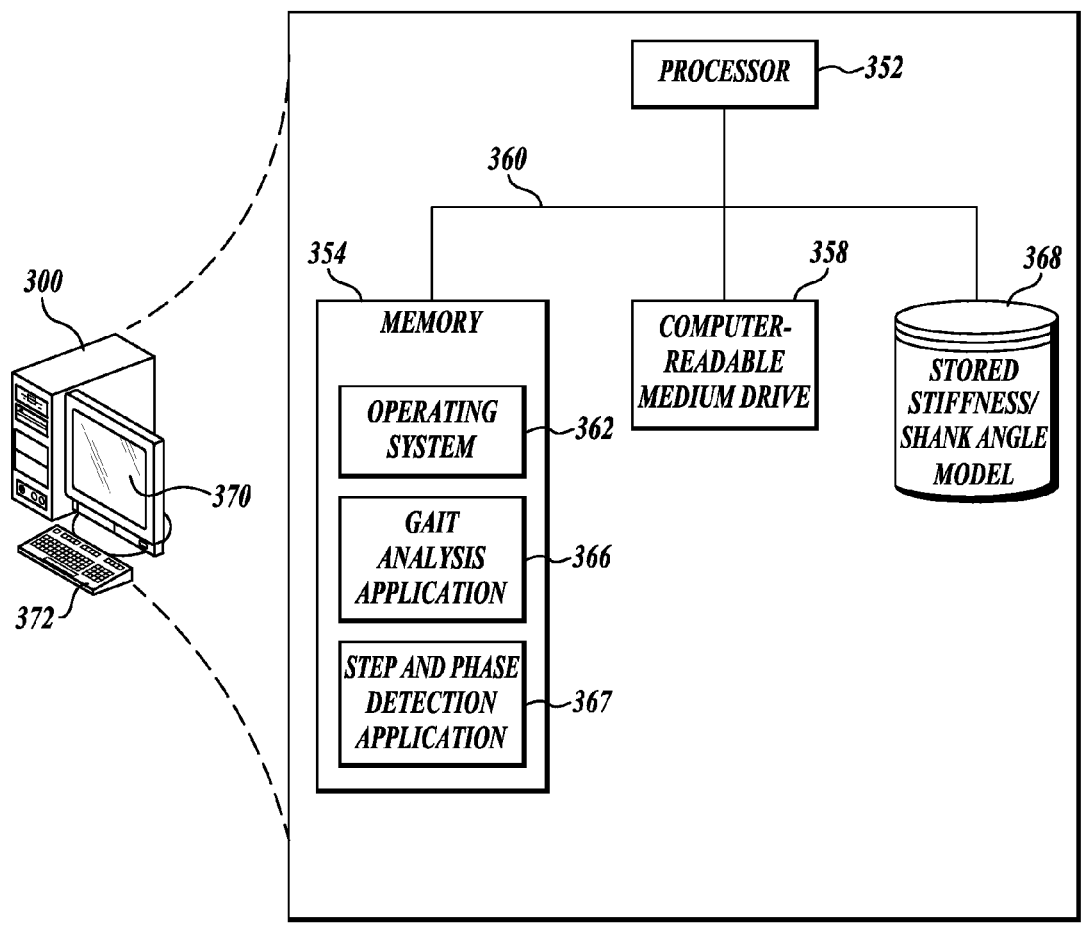
FIG. 4 is a schematic illustration of a computer for the computerized orthotic prescription system.

FIG. 4 illustrates an exemplary computer 300 with components that are capable of implementing a method to prescribe an orthosis by conducting "gait analysis" using a gait analysis application 366 and a phase and step detection application 367 and providing feedback to the user 324 to achieve a suitable orthosis stiffness and/or shank angle. Those skilled in the art will recognize that the computer 300 may be any one of a variety of devices including, but not limited to, personal computing devices, server-based computing devices, mini and mainframe computers, laptops, or other electronic devices having some type of memory. Those skilled in the art will also recognize that the more than one computer can be used in place of a single computer. Furthermore, the functions performed by the computer 300 may be distributed or shared among more than one computers that are all communicatively linked, such as via local area networks (LAN), wide area networks (WAN), and/or the Internet. The computer 300 depicted in FIG. 4 includes a processor 352, a memory 354, a computer-readable medium drive 358 (e.g., disk drive, a hard drive, CD-ROM/DVD-ROM, etc.), that are all communicatively connected to each other by a communication bus 360. The memory 354 generally comprises Random Access Memory ("RAM"), Read-Only Memory ("ROM"), flash memory, and the like. The host computer 300 also includes a display 370 and one or more user input devices 372, such as a mouse, keyboard, etc.

As illustrated in FIG. 4, the memory 354 stores an operating system 362 for controlling the general operation of the computer 300. The operating system 362 may be a special purpose operating system designed for the computerized orthotic prescription system. Alternatively, the operating system 362 may be a general purpose operating system, such as a Microsoft® operating system, a Linux operating system, or a UNIX® operating system. In any event, those skilled in the art and others will recognize that the operating system 362 controls the operation of the computer 300 by, among other things, managing access to the hardware resources and input devices. For example, the operating system 362 performs functions that allow a program to receive data wirelessly through a modem 312 or over a radio receiver and/or read data from the computer-readable media drive 358. As described in further detail below, moment and axial force data in real time may be made available to the computer 300 from the computer-readable medium drive 358. In this regard, a program installed on the computer 300 may interact with the operating system 362 to process the data received from the computer-readable media drive 358.

As further depicted in FIG. 4, the memory 354 additionally stores program code that provides a gait analysis application 366 and a step detection application 367. The gait analysis application 366 includes computer-executable instructions that, when executed by the processor 352, applies an algorithm to receive, display, and process input, including moment and axial force data, to assist the user 324 in determining the stiffness and/or shank angle of a orthosis. The gait analysis application 366, among other things, applies an algorithm to a set of moment data to an optimal model of stiffness and/or shank angle stored on a device 368. The step and phase detection application 367 applies an algorithm to a set of moment and axial force data to determine if the orthosis is being used in steady state walking, and if it is, the algorithm differentiates each step and extracts the moment data during the stance phase. The stance phase is a phase of walking defined as the initial contact of the heel with the ground ending with toe-off the ground. Further, the step and phase detection application 367 establishes if the orthosis is either in stance or swing phase of a gait cycle. A step, for any one foot, can be defined from one heel contact to the next heel contact, and thus, includes a stance phase (in contact with the ground) and a swing phase (no contact with the ground).

Figure 5:
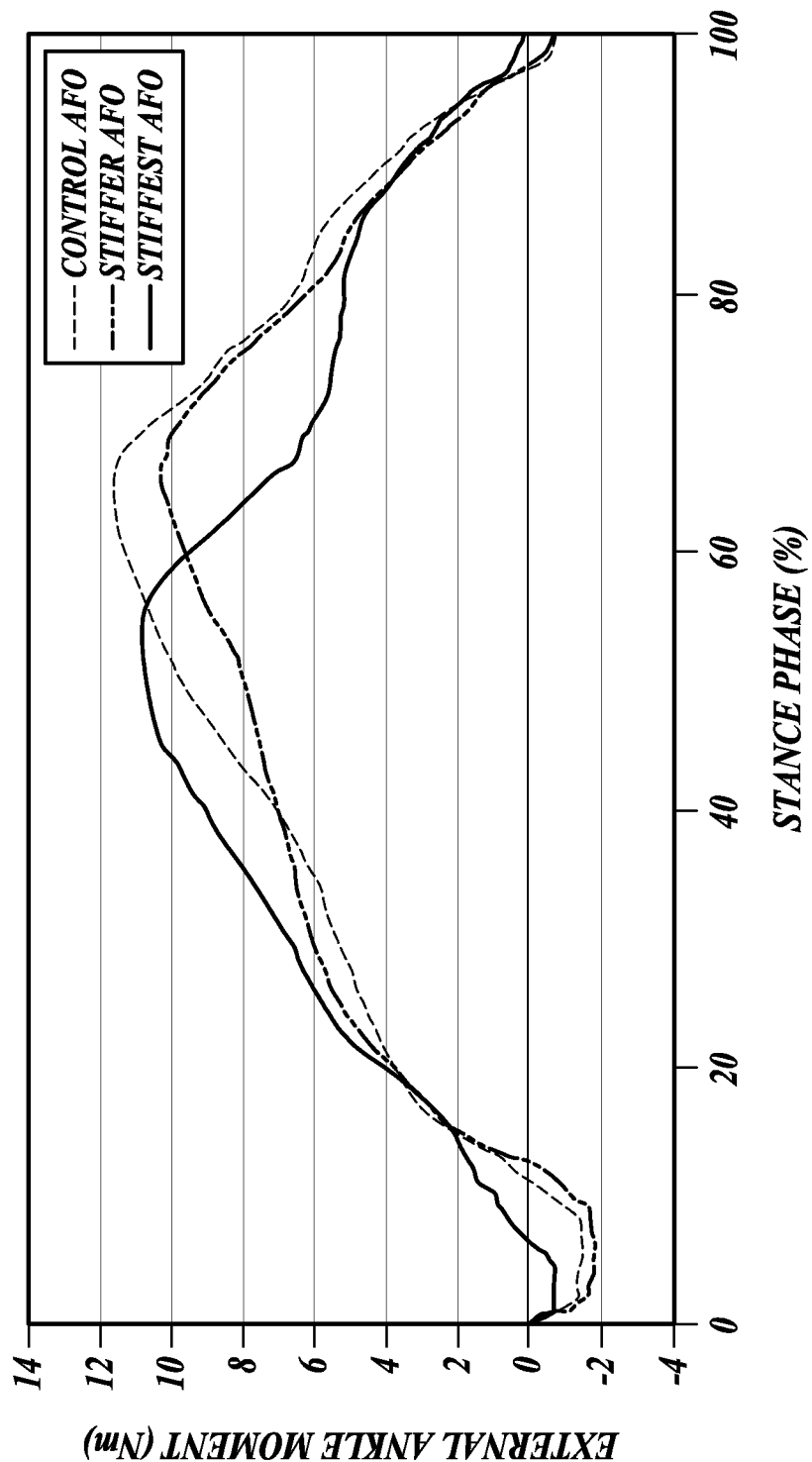
FIG. 5 is a graph illustrating the correlation of AFO stiffness and/or shank angle on ankle joint moments during a stance phase.

Referring to FIG. 5, graphs showing exemplary plots of the ankle moments measured using AFOs with various degrees of stiffness and/or shank angle, are illustrated. It has been found that the ankle moments (i.e., external forces that tend to rotate the ankle in a dorsiflexion or plantarflexion fashion when the foot is in contact with the ground) are dependent on the stiffness and/or shank angle of an orthosis. Thus, it has been determined that compiling ankle moment data of "good" subjects with correct ankle function into a model, and then comparing ankle moments from a patient wearing an orthosis to such model, one can determine whether the orthosis is correctly tuned, i.e., of the correct stiffness and/or shank angle. The comparisons may also be used to decide whether the orthosis is too stiff or not stiff enough and/or whether shank angle has the proper degree of angle. And even further, applications can be created that can provide a recommendation for how to tune the orthosis to match the model. As shown in FIG. 5, the AFO with a control stiffness (dashed line) is compared against two AFOs with a higher degree of stiffness, including a stiffer AFO (dashed and dotted line) and the stiffest AFO (continuous line). While shown as a curve including a single "y" axis value, the curves can be plots of averages, or curves may be plotted as bands having an upper and lower curve that indicate the expected changes in ankle moment with changes in orthosis shank angle alignment and/or stiffness. Comparisons are made by statistical algorithms that determine the closeness of the real data to the model data. The methods disclosed herein use this principle to assist orthotists in prescribing a correctly tuned orthosis. This method has applications beyond AFOs, and may be used for any other type of orthosis. Additionally, this method may be used for tuning orthoses used for knees and hips.

Figure 6:
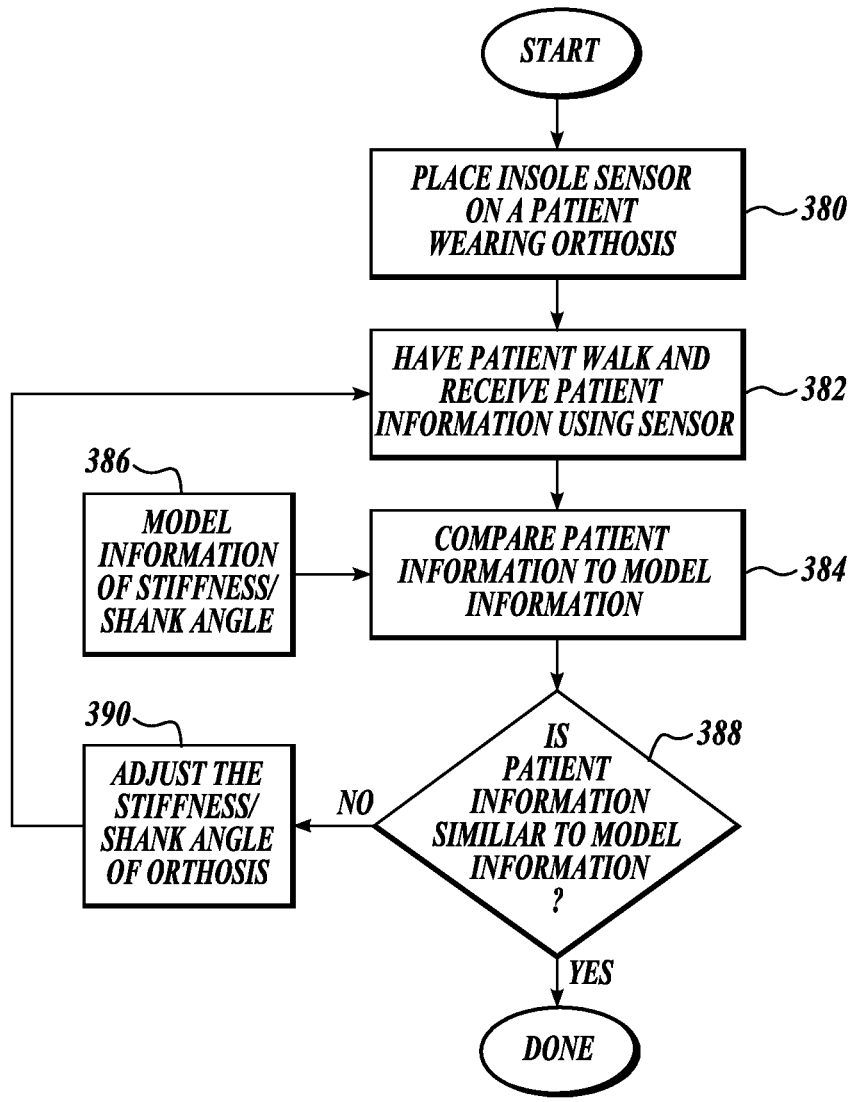
FIG. 6 is a flow diagram illustrating a method of determining whether orthosis stiffness and/or shank angle is correct.

Referring to FIG. 6, a general method for prescribing stiffness and/or shank angle of an orthosis using the computerized orthotic prescription system, is illustrated. The method begins with mounting the sensor 302 to an orthosis or inside a shoe of a patient, block 380. From block 380, the method enters block 382. In block 382, the sensor 302 sends, and the computer 300 receives patient information. Patient information may also include weight and other patient physical characteristics. Such information may come from sensor 302 or, alternatively, input from the user. From block 382, the method enters block 384. In block 384, the computer 300 receives model information, block 386, and compares, via the use of statistical algorithms, the patient information to the model information. From block 384, the method enters block 388. In block 388, the computer 300 applies algorithms to make decisions whether the patient information is similar to the model information, such that the orthosis may be considered to be properly tuned, correct, or optimal with respect to stiffness and/or shank angle, and may further recommend a corrective action.

A properly tuned, correctly tuned, or optimal orthosis minimizes gait deviations caused by the physiological loss of muscle power or control from disease or trauma. This is achieved by optimizing the dynamic stability and kinematics of the patient for efficiency and safety. This dynamic stability is altered by changing the apparent stiffness of the joints of the limb and their position. In one embodiment of an AFO, this means altering both ankle stiffness and shank angle to provide tolerable ground reaction forces necessary for support of the body during stance phase and clearance of the foot during swing phase.

If the determination in block 388 is "yes," the method is completed. If the determination in block 388 is "no," the method enters block 390. In block 309, the orthotist may adjust the stiffness and/or shank angle of the orthosis, allow the patient to walk using the newly adjusted orthosis, and the method returns to block 382. The method of FIG. 6, may be implemented, in part, on one or more computers. Additionally, a tangible computer-readable medium, such as CD, and any memory device, may be coded with instructions for performing steps of the method of FIG. 6.

FIGS. 7-11 describe one specific embodiment of performing a method for prescribing the stiffness and/or shank angle of an orthosis to achieve a properly tuned orthosis with respect to stiffness and/or shank angle. The method of FIGS. 7-11, may be implemented, in part, on one or more computers. More specifically, the method may be implemented by software in the computer memory 354, stored as the gait analysis application and the step and phase detection application. Additionally, a tangible computer-readable medium, such as CD, and any memory device may be coded with instructions for performing steps of the method of FIGS. 7-11.

Figure 7:
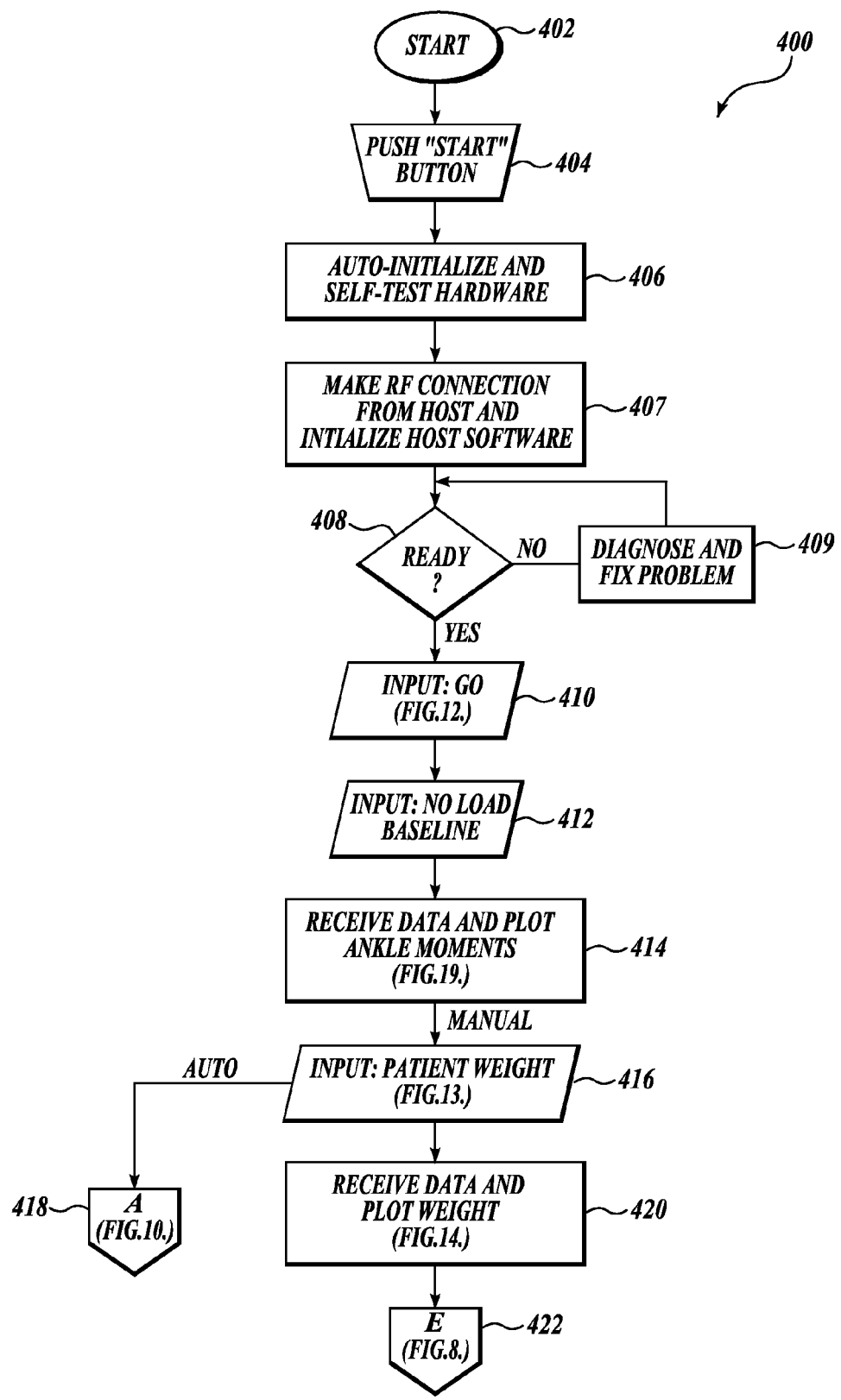
FIG. 7 is a flow diagram illustrating a method of determining whether orthosis stiffness and/or shank angle is correct.

Referring to FIG. 7, a method 400 for prescribing the stiffness and/or shank angle of an orthosis using the computerized orthotic prescription system, is illustrated. The method 400 begins at start block 402. It is to be understood that the patient has been fitted with the sensor 302 and the orthosis 304 (FIG. 2) for the method to operate. From start block 402, the method 400 enters block 404. In block 404, the user 324 may be requested to push a "start" button that activates the computerized orthotic prescription system. The "start" button can be a physical button or a software button on a graphical user interface displayed on the computer 300. From start block 402, the method 400 enters block 406. In block 406, the computerized orthotic prescription system auto initializes itself and performs a self test on the hardware including the sensor 302. The automatic test of the system hardware will only take about one second. From block 406, the method 400 enters block 407. In block 407, the sensor 302 makes a radio frequency connection to the computer 300 and the computer's 300 software is initialized. The computer 300 may perform automatic calibration of the sensor 302. The status of the startup process may be monitored by observing indicators on a graphical user interface appearing on the computer's display 370. The computerized orthotic prescription system is designed to signal if there is a problem. For example, an indication of low battery power may be provided. If there are no problems, a status indicator may turn green.

From block 407, the method 400 enters block 408. In block 408, a determination is made whether the computer 300 is ready to receive patient information. If the determination in block 408 is no, the method 400 enters block 409. In block 409, the user 324 may diagnose and fix the problem with the hardware and/or software of the computerized orthotic prescription system, and from block 409, the method 400 reenters block 408. If the determination in block 408 is yes, meaning that the computerized orthotic prescription system 100 is ready, the method 400 enters block 410. In block 410, the computerized orthotic prescription system 100 receives input, such as "go" from the user 324. The user 324 can graphically push a "go" button on the graphical user interface displayed by the computer 300. See, for example, FIG. 13, button 802, which has been activated. Once "go" is pushed, the button may then change labels into a "stop" button. The computer 300 will then start to receive patient information from the sensor 302. The user 324 may interact with the computer 300 via the graphical use interfaces, embodiments of which will be described below in association with FIGS. 12-19. From block 410, the method 400 enters block 412. In block 412, the computerized orthotic prescription system receives input from the user 324 for the no-load base line. The no-load base line refers to the readings from the sensor 302 measured when the patient 326 is not applying any weight on the sensor 302. With the computerized orthotic prescription system running, the patient 326 can raise his or her foot so that it is slightly off the floor. The user 324 can then zero the sensor 302 to establish the no-load base line for the sensor 302. In one embodiment of the method 400 and system, the method and system may be in one of three modes: setup mode, static mode, and dynamic mode. See, for example, FIG. 18, showing the three modes.

The actions corresponding to each respective mode will be described below. Any mode may be entered from any other mode. Modes may occur simultaneously or may be entered in series and in any order. The user 324 may request, via the graphical user interface, to manually enter any mode; or upon completion of an action, any mode may be entered automatically, for example, by receiving a signal from a sensor, or upon completion of a step. In general, setup mode refers to the entry of input from the user 324 via the graphical user interface in preparation for receiving patient information. Static mode generally refers to real time monitoring and receiving of patient information produced from the sensor 302 output while the patient 326 is standing. In the static mode, for example, the gait analysis application 366 may provide static "balance" information by supplying forces in real time. A real time weight graph may also be provided and may be used as biofeedback to show the patient 326 how much of their weight is being supported by the foot with the orthosis. Static mode may also include providing the opposite foot loading if the patient's 326 weight has been entered at some point in the setup mode. In dynamic mode, the patient 326 will begin to walk, and the system will receive ankle moment information and perform analysis for determining when the stance phases are occurring so that the ankle moment information is correlated to the stance phase.

Returning to FIG. 7, from block 412, the method 400 enters block 414. In block 414, the computer 300 begins to receive patient information and the computer 300 plots the moments on the computer display 370. See, for example, FIG. 19. The computer display may also include a plot of the model information provided simultaneously with the real time moment information from the patient. In this way, the user 324 obtains a visual picture of the closeness of the orthosis to the model.

From block 414, the method 400 enters block 416. In block 416, the gait analysis application 366 receives the patient's weight. The patient weight input may be obtained via an automatic algorithm or via a manual input from the user 324. See, for example, FIG. 13 for a graphical use interface to input weight manually. If the patient weight input is obtained manually, i.e., the user 324 can, via the graphical user interface, enter the weight of the patient 326. Thereafter, the method 400 enters block 420, wherein the host computer 300 begins receiving weight data from the sensor 302 and plotting the weight data in a display. Naturally, the weight sensed by the sensor 302 only measures the weight sensed by the foot with the sensor 302. See, for example FIG. 14. If the patient weight input is obtained automatically, the method 400 enters the automatic patient weight input subroutine 500 beginning in block 418. The automatic patient weight input subroutine 500 will be described with reference to FIG. 10.

Figure 9:
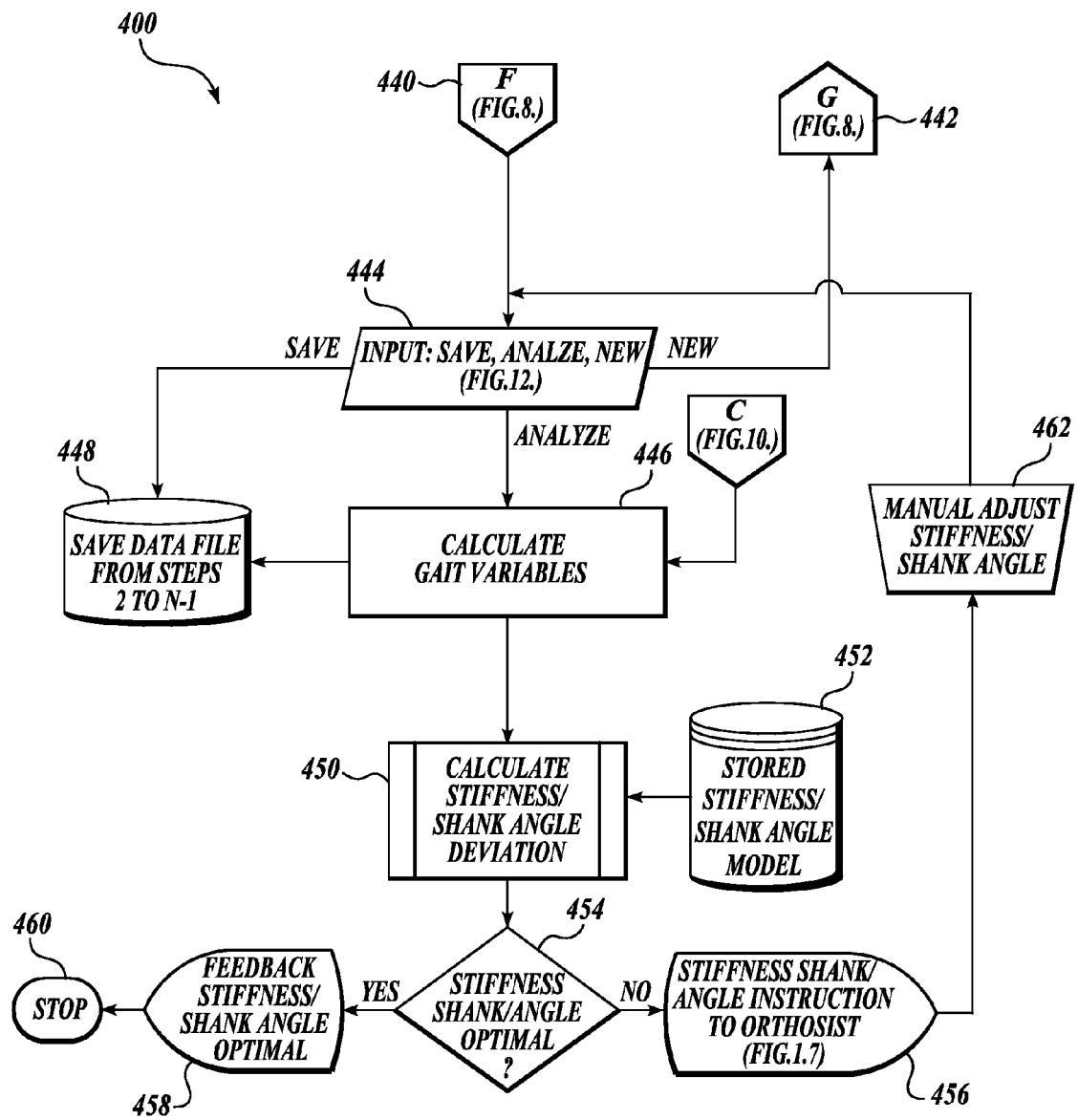
FIG. 9 is a flow diagram illustrating a method of determining whether orthosis stiffness and/or shank angle is correct.
Figure 10:
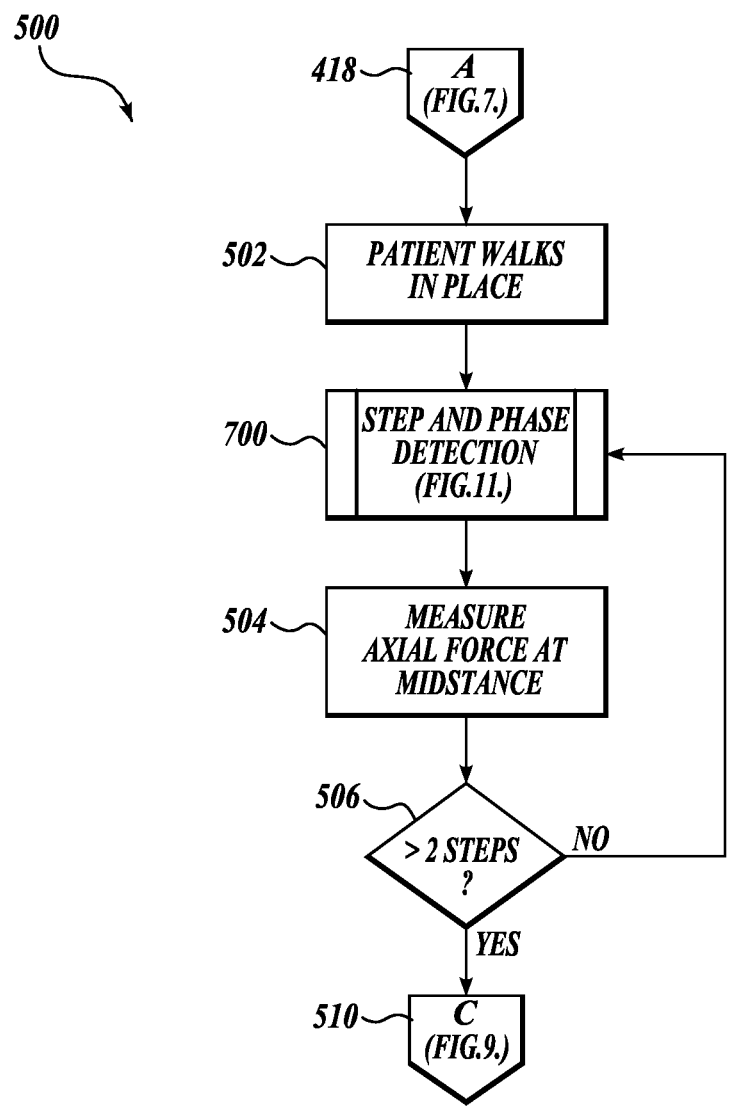
FIG. 10 is a flow diagram illustrating a method of determining whether orthosis stiffness and/or shank angle is correct.

Referring to FIG. 10, the automatic patient weight input subroutine 500 begins at block 418. From block 418, the automatic patient weight input subroutine 500 enters block 502. In block 502, the patient 326 is asked to walk in place. From block 502, the automatic patient weight input subroutine 500 enters block 700. Block 700 is a method for calling up the step and phase detection application 367. The step and phase detection application determines the stance phase, i.e., when a foot is in contact with the ground. From information provided by the sensor 302, the step and phase detection application is able determine the start (0%), mid-stance (50%), and end (100%) of a stance phase from the initial contact of the heel to toe-off the ground. The weight is determined when the patient reaches mid-stance, since the patient's center of gravity is directly over the sensor. From block 700, the automatic patient weight input subroutine 500 enters block 504. In block 504, the automatic patient weight input subroutine 500 measures the axial force at the mid-stance of the stance phase of the step. From block 504, the automatic patient weight input subroutine 500 enters block 506. In block 506, a determination is made whether greater than two steps have been completed. The automatic patient weight subroutine 500 can use one step to gather the weight information; however, two or more steps can be used, and the average taken to have a more reliable weight measurement. The automatic patient weight input subroutine 500 can keep track of the number of steps by counting the number of initial contacts, toe-offs, or both. If the determination in block 506 is no, the automatic patient weight input subroutine 500 returns to block 700. If the determination in block 506 is yes, the automatic patient weight input subroutine 500 enters block 508. In block 508, the axial force at the mid-stance measured from more than two steps is calculated and used in the orthotic prescription method 400 in blocks 416 (FIG. 7) or block 446 (FIG. 9).

Returning to FIG. 7, after the patient weight is input either through manual input or through automatic input, the method 400 enters a continuation block 422. Continuation block 422 indicates the method 400 is continued on FIG. 8.

Figure 8:
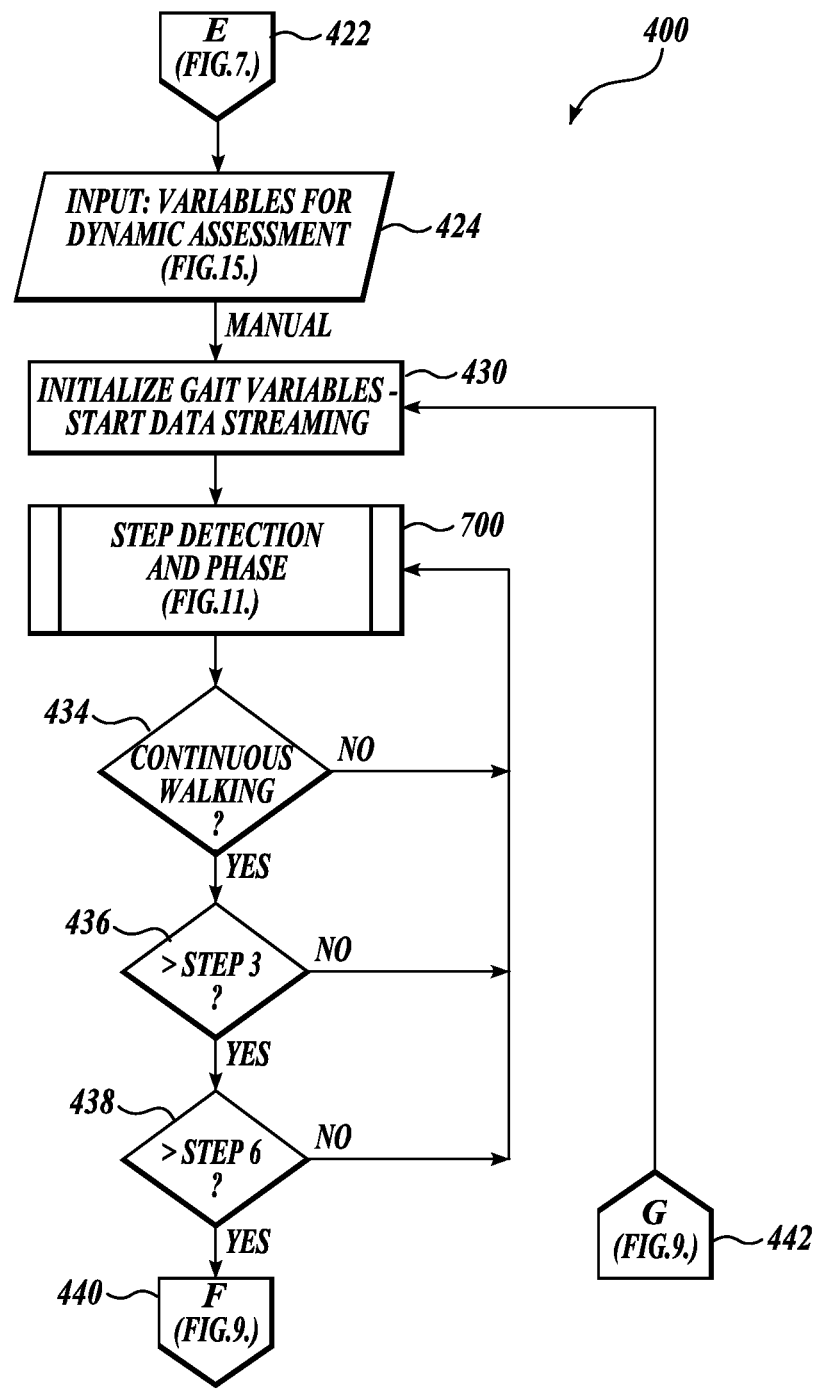
FIG. 8 is a flow diagram illustrating a method of determining whether orthosis stiffness and/or shank angle is correct.

Referring to FIG. 8, continuation block 422 from FIG. 7 is followed by block 424. In block 424, variables for dynamic assessment of stiffness and/or shank angle are input. The variables may include the client identifier, the type of orthosis, for example, FO, AFO, KAFO, and HKAFO, whether the left or right leg is being measured, the client weight, and the distance of a horizontal line from a reference point, such as the posterior of the heel to the axis of the joint movement, and the shank angle in degrees measured between the Achilles portion 106 (or 114) and the sole 102 (or 116). Some or all of these variable are used by the gait analysis application to develop a more robust model. For example, based on the patient weight, the model can be derived only from samples approximately the same weight as the patient. Additionally or alternatively, the model can be normalized for the patient. The gait analysis application 366 may provide a graphical user interface for the purpose of entering variables. See, for example, FIG. 15.

From block 424, the method 400 enters block 430. In block 430, the method 400 initializes the gait variables and starts streaming patient information to the computer 300. Gait variables are characteristics of gait, i.e., the manner of walking. At this point in the method 400, the gait analysis application 366 may bring up a graphical user interface providing the user 324 with selection buttons including: go/stop, new, analyze, and save. See, for example, FIG. 18. Generally, the user 324 is prepared to select the go button to allow streaming data from the sensor 302 to the computer 300. While the data is streaming, the graphical user interface labels the button as a stop button.

Figure 11:
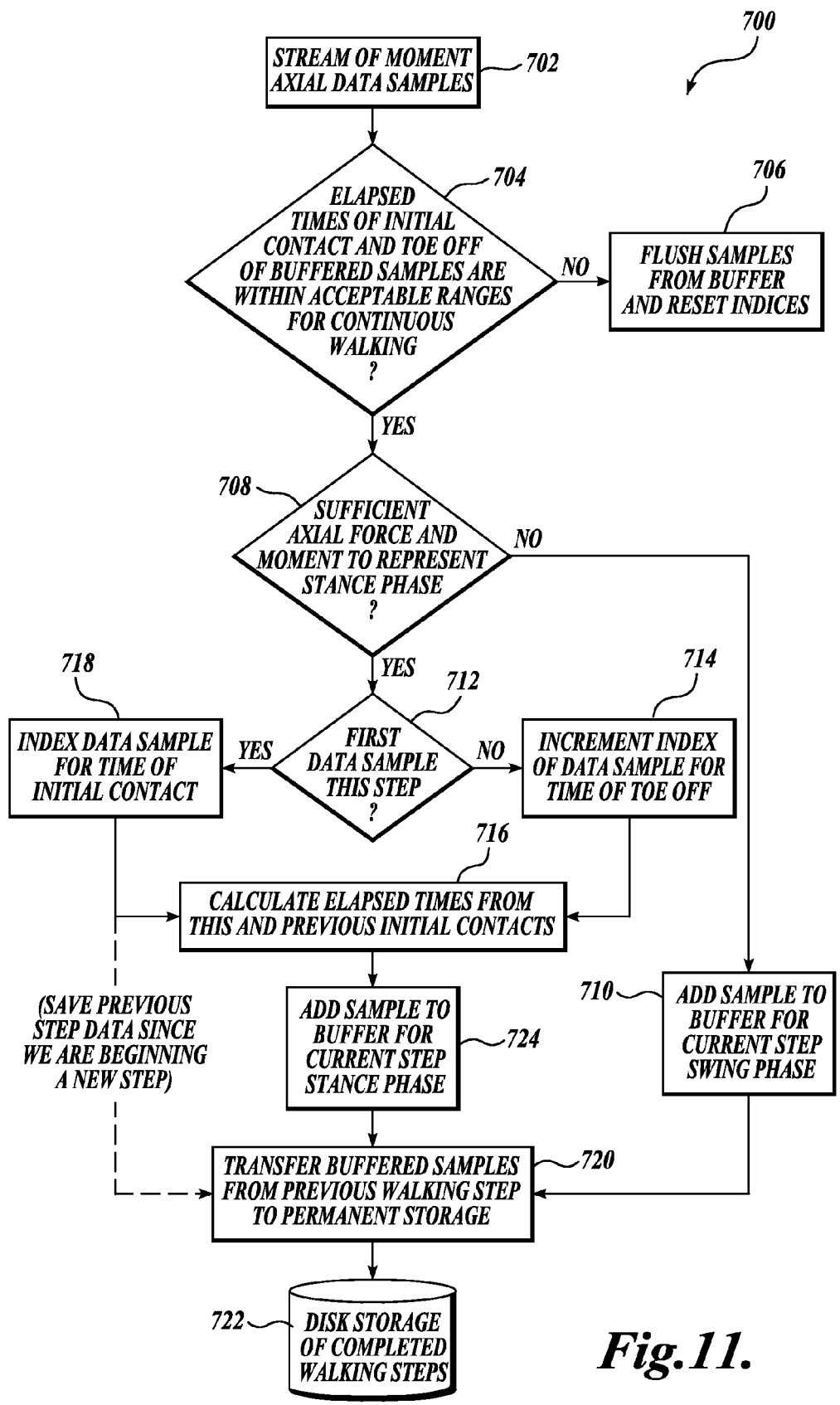
FIG. 11 is a flow diagram illustrating a method of determining whether orthosis stiffness and/or shank angle is correct.

For more accurate analysis, consistency should be strived for; therefore, moment data is preferably collected from more than one step of a continuous walking session during which the patient 326 does not pause or otherwise interrupt his or her gait. This minimizes any effects caused through acceleration and deceleration. In one embodiment, a continuous walking session includes at least 3 steps in series, but need not be greater than 6 steps. Alternatively, at least 2 steps may be used, or in some instances a single step. Additionally, data may be collected from more than one step, and steps that have similar characteristics are used in analysis, while the dissimilar steps are discarded. Data gathered during walking includes forces or moments experienced by the ankle joint during the stance phase of each step, as measured by the sensor 302. The step and phase detection algorithm 700 is employed to determine the start and stop of each step and of each phase of each step, and thus allows counting the number of steps during the session, and also determines the midstance (50% of stance phase) for calculation of the axial forces indicative of the patient's weight. By using the readings of moments and axial force, the step and phase algorithm 700 is able to identify discrete phases of the gait cycle, such as the stance and swing phase of each foot, when they occur in time, and determine whether continuous walking is occurring. This collection of data and counting of steps is described in FIG. 8 as blocks 700, 434, 436, and 438. From block 430, the method 400 enters block 700. Block 700 is the step and phase detection algorithm that is illustrated in FIG. 11. From block 700, the method 400 enters block 434. Block 434 is for determining whether continuous walking is occurring. If the determination in block 434 is no, the method 400 returns to block 700, the step and phase detection algorithm 700. If the determination in block 434 is yes, the method 400 enters block 436. In block 436, the method 400 determines whether greater than three steps have been completed. If the determination in block 436 is no, the method 400 returns to block 700. If the determination in block 436 is yes, the method 400 enters block 438. In block 438, the method 400 determines whether greater than six steps have been completed. If the determination in block 438 is no, the method 400 returns to block 700. If the determination in block 438 is yes, the method 400 enters a continuation block 440. Continuation block 440 indicates that method 400 is continued in FIG. 9.

Referring to FIG. 9, from continuation block 440, the method 400 enters block 444. After collecting data, the method 400 awaits the user's 324 input. Block 444 is for receiving input from the user 342. The gait analysis application 366 brings up a graphical user interface for providing options for the user 324. See, for example, FIG. 18. The graphical user interface may have "save," "analyze," and "new" buttons that the user 324 may select to save data, analyze data, or perform new data collection. The user 324 may click on the new button to start collecting data from a new series of steps. Generally, the user 324 will select the new button before the patient 326 starts to walk. The new button is also selected whenever a change has been made to the stiffness and/or shank angle of the orthosis and the user 324 would like to remeasure with the newly adjusted orthosis. If the user 324 selects the save button, the data can be saved to memory, and recalled for a later time. The user 324 may start a new session by selecting the new button so that the gait analysis application 366 then starts looking for a "new" series of steps to record once the patient 326 starts walking again. Once six steps have been recorded, the gait analysis application 366 will not add additional steps. This limit of steps is variable, six being merely representative of one embodiment. The gait analysis application 366 may use as little as one step. The user 324 may select the analyze button to analyze the current data or select a set of data from an earlier saved session, or may even select a session from a different patient. The gait analysis application 366 may set a condition on whether to enable the analyze button. For example, the gait analysis application 366 may enable the analyze button when a minimum number of continuous steps are collected in series. A suitable number for analysis is four, but fewer or more steps may also be used, four being merely representative of one embodiment.

The options for the user 324 are represented by block 444. From block 444, if the input to block 444 is "save," the method 400 enters block 448. In block 448, the method 400 saves into a data file, data collected from steps 2 to n−1. The first step may be thrown out, as well as the last step, since these steps are not nearly as representative of normal continuous walking as the steps in-between. If the input in block 444 is "new," the method 400 returns via continuation block 442 to FIG. 8. Referring to FIG. 8, from continuation block 442, the method 400 returns to block 430. If the input in block 444 is "analyze," the method 400 enters block 446. In block 446, the method 400 calculates gait variables from the sensor data. From block 446, the method 400 enters block 450. In block 450, the method 400 calculates the deviation of the orthosis stiffness and/or shank angle compared to the model.

The gait analysis application 366 analyzes the patient's gait relative to a model 368 by comparing the patient's gait variables when using the orthosis to gait variables of a correct or optimal gait stored in the computer 300. The gait analysis application 366 determines deviations in the patient's gait variables from the model gait variables. These deviations are a function of the orthosis stiffness and/or shank angle. Relationships have been predetermined between orthoses that are stiffer or weaker or have different shank angles as compared to the model created from prior data sampling. See, for example, FIG. 5. From this comparison, the gait analysis application 366 can determine whether the orthosis is too stiff, not stiff enough, or correctly stiff, as well as also determine whether the shank angle is too small or to large, in comparison to a model complied from samples of patient's with correct stiffness and/or shank angles. The information for building the model may be collected from a training set of data of persons who have a correct or optimal ankle stiffness and/or shank angle. For example, the sensor 302 can be inserted into the shoes of a variety of persons determined to have a correctly functioning ankle. The more sampling that is done, the more robust the model can be. When all the sample data is collected, it can be normalized so that it may be used to compare to any patient. From block 450, the method 400 enters block 454. In block 454, the method 400 determines whether the present orthosis stiffness and/or shank angle is optimal by performing a comparison of the gait variables for the present session as compared with the stiffness/shank angle model 368. The stiffness/shank angle model block 452 supplies the stiffness/shank angle model to the comparison block 450.

To analyze for the deviation of the orthosis stiffness and/or shank angle against the model stiffness/shank angle, the gait analysis application 366 calculates for each individual step, certain gait variables. Gait variables may include, but are not limited to some or all of the anterior/posterior moment and right/left moment at each 20 percent increment of the stance phase from 0% to 100%; the maxima and minima of the anterior/posterior moment and right/left moment for the first and the last 50% of the stance phase; the slope of the change in anterior/posterior moment and right/left moment during each successive 20% stance increment; and the integrated anterior/posterior moment and right/left moment measured over the period of each stance phase. The integrated moment is an accumulated moment value over a period of time.

The equations used in deriving the stiffness/shank angle model are derived heuristically to minimize an external criterion called the Prediction Error Sum of Squares, or PESS, for previously measured ankle joint moments.

$$PESS = \frac{1}{N}\sum_{t=1}^{N}(y_t - f(x_t, \hat{a}_t))^2$$

Where N is the number of gait variable samples available, y is the target stiffness or the shank angle, and a is an estimation of the combined parameters that describe the stiffness or shank angle. The equation derivations are achieved using the Group Method of Data Handling described by Madala and Ivakhnenko (Madala, H., and Ivakhnenko, A., "Inductive Learning Algorithms for Complex Systems Modeling," CRC Press, Boca Raton, Fla., USA, 1994). Solving the derived model equations with the gait variables calculated from the computerized orthotic prescription system data, results in a numeric estimation of the stiffness and shank angle in the orthosis measured. For robustness, estimations from each of the equations becomes a vote added to a more generalized estimation of the stiffness and shank angle.

Returning to FIG. 9, if the determination in block 454 is no, meaning that the stiffness and/or shank angle is not optimal or correct, the method 400 enters block 456. In block 456, the gait analysis application 366 may provide verbal, textual, or graphic instructions to the user 324 to make the stiffness and/or shank angle of the orthosis similar to the optimal stiffness/shank angle model from block 452. Such corrective action can be provided to a user 324 via the computer's 300 display 370 or, alternatively, the computer 300 may issue verbal instructions. See, for example, FIG. 17. In another embodiment, the computer 300 may display the model and the patient data on one graph so that the user 324 can visually compare how far or close the patient information is to the model information.

Figure 1A:
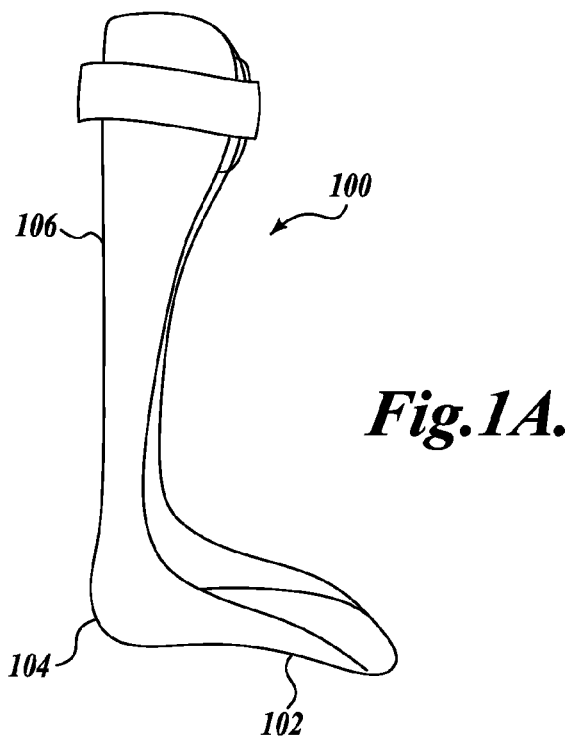
FIG. 1A is a diagrammatical illustration of an AFO.
Figure 1B:
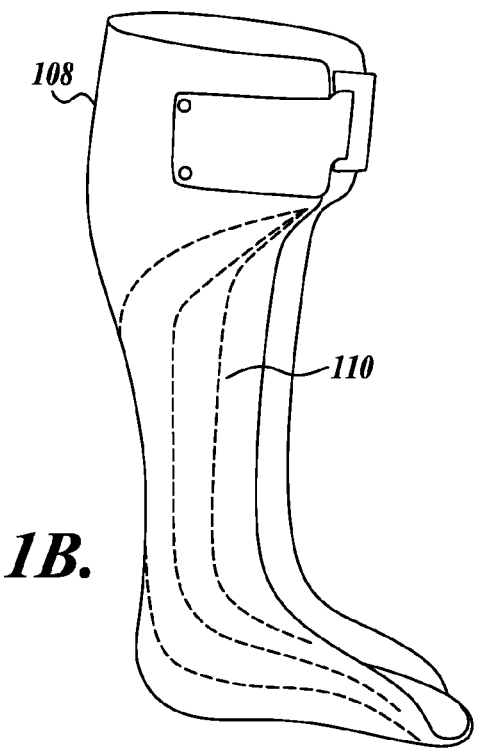
FIG. 1B is a diagrammatical illustration of an AFO.
Figure 1C:
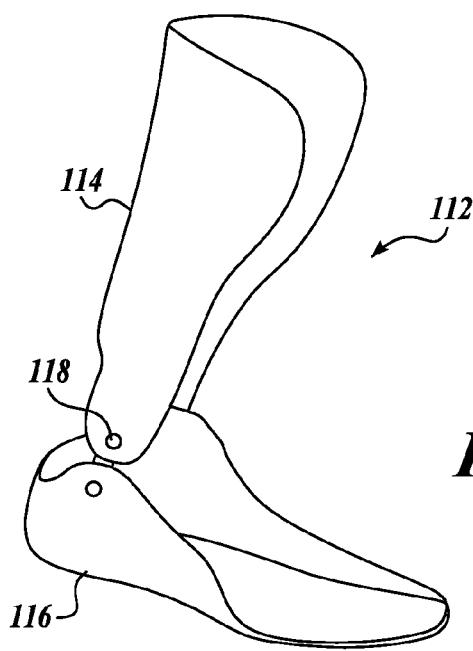
FIG. 1C is a diagrammatical illustration of an articulated AFO.

From block 456, the method 400 enters block 462. In block 462, the user 324 manually adjusts the stiffness and/or shank angle of the orthosis by either cutting more material from the orthosis at a deeper trim line (FIG. 1B) or changing a parameter at the pivot joint of the articulated orthosis (FIG. 1C). From block 462, the method 400 enters block 444, where the user can save, analyze, or start a new data collection trial.

If the determination in block 454 is yes, meaning that the stiffness and/or shank angle is optimal or correct, the method 400 enters block 458. In block 458, the method 400 indicates to the user 324 that the stiffness and/or shank angle of the orthosis is optimal or correct and no further corrections are necessary. From block 458, the method 400 enters block 460, where the method 400 ends with a correctly tuned orthosis.

In another embodiment, the patient need not be in a clinical setting to have an analysis of the orthosis stiffness and/or shank angle. The sensor 302 may remain incorporated in the orthosis, and the patient 326 may use the orthosis with the included sensor 302 in the normal course of walking for an extended period of time. During such extended period of time, the sensor 302 may continuously or semi-continuously record the forces, i.e., the anterior/posterior, right/left moments, axial force, and any other data and store the information in the onboard memory 208. At a later time, the information from the onboard memory 208 may be retrieved and analyzed.

Referring to FIG. 11, a flow diagram for the step and phase detection application 367 is illustrated. The step and phase detection application will be described in the context of a method 700. Generally described, the step and phase detection application 367 uses information from the sensor 302 to determine whether the patient is walking, determine whether walking is generally constant to able to obtain good data for comparison to the model, and further determine when a stance phase is occurring. The information may be analyzed in real time. The method 200 begins at block 702. In block 702, the method obtains a stream of moment and axial force data from the sensor 302. From block 702, the method 700 enters block 704. In block 704, a determination is made whether the elapsed times of the initial contact and toe-off of steps are within acceptable ranges to define continuous walking. If the elapsed times are too long, indicating either standing or slow walking, or too short, indicating running, then the program enters block 706. In such case, the data sample is not from steady state walking, and the method enters block 706 where the data sample is removed from memory. The gait variables are reset. If the determination in block 704 is yes, the method 700 enters block 708. In block 708, the method 700 determines whether the axial force is greater than a threshold. This is so the method may determine if the patient is in the stance phase. If the determination is yes, then the data sample is considered to be within a stance phase and the method 700 enters block 712. If the determination is no, the method 700 considers the data sample to be from the swing phase and the method 700 enters block 710. Data can stream at several times per second so that during each step, several data streams can be sent. The data identifying the start of the stance phase is determined by the step and phase detection application 367. For example, by determining when the axial force is above a threshold. In block 712, if the data sample is the first sample, then the data sample is indexed and identified with the initial contact time in block 718, otherwise the sample is assigned to be the last sample and is indexed as toe-off temporarily in block 714. Thereafter, each data sample will be assumed to be the last sample and is assigned the index of the toe-off sample in block 714. The last data sample is added to a buffer containing samples of the current step stance phase. On the next occurrence of a data sample being in stance phase (Initial Contact), the completion of the previous step is marked by transferring the buffered samples to an indexed array of completed individual steps and phase indices in block 720. This facilitates analysis by the gait analysis application 366 by permanently storing the data on the computer readable medium in block 722. In block 708, the step and phase detection application 367 may set a lower threshold of axial force below which the stance phase is not detected. If the determination in block 708 is no, the method 700 enters block 710. In block 710, the method 700 adds the data sample to a buffer and identifies it as a swing phase. From block 718, the method 700 may enter block 716 or block 720. Block 720 is entered when the data sample comes from a new step. The data from the previous step is saved. In block 720, the method 700 transfers buffered data samples from the previous walking step to permanent storage. Block 716 is entered always when the data is from a stance phase, regardless of whether it is the first or last sample. In block 716, the elapsed time is calculated from the current and previous initial contact. Block 716 generally assigns a time to the data sample. From block 720, the method 700 enters block 722. In block 722, the method stores the data for the completed walking steps.

The step and phase detection application 367 and the gait analysis application 366 uses graphical user interfaces for interacting with the user 324. Embodiments of the graphical user interfaces are illustrated in FIGS. 12-18.

Figure 12:
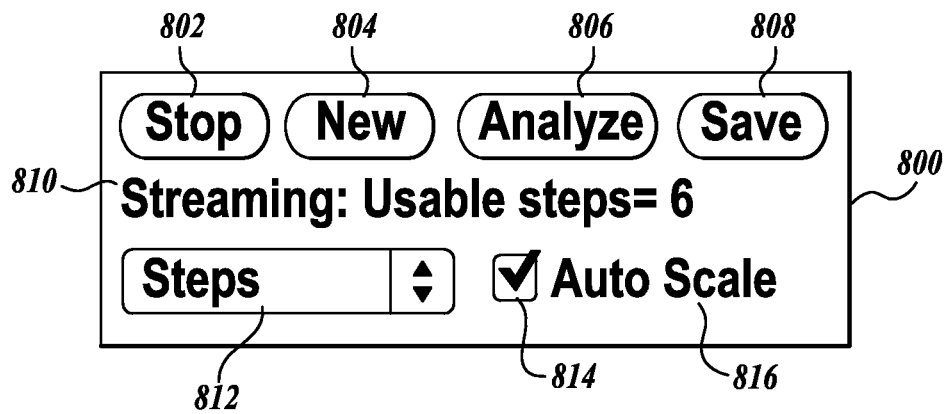
FIG. 12 is a diagrammatical illustration of a graphical user interface.

FIG. 12 illustrates a graphical user interface 800 provided by the gait analysis application 366 for use in block 410 of method 400 in FIG. 7. The graphical user interface 800 provides to the user 324, the option to select from four buttons, including a go/stop button 802, a new button 804, an analyze button 806, and a save button 808. The graphical user interface 800 also includes a drop down menu 812 for selecting the number of steps to plot and a label 810 and text box showing the number of usable steps during streaming. The graphical user interface 800 also includes a check box 814 and label 816. The label 816 identifies the check box 814 is for auto scaling the plots of the moments. By clicking on the auto scale checkbox 814, the user 324 can automatically scale the graphs to a suitable range.

Figure 13:
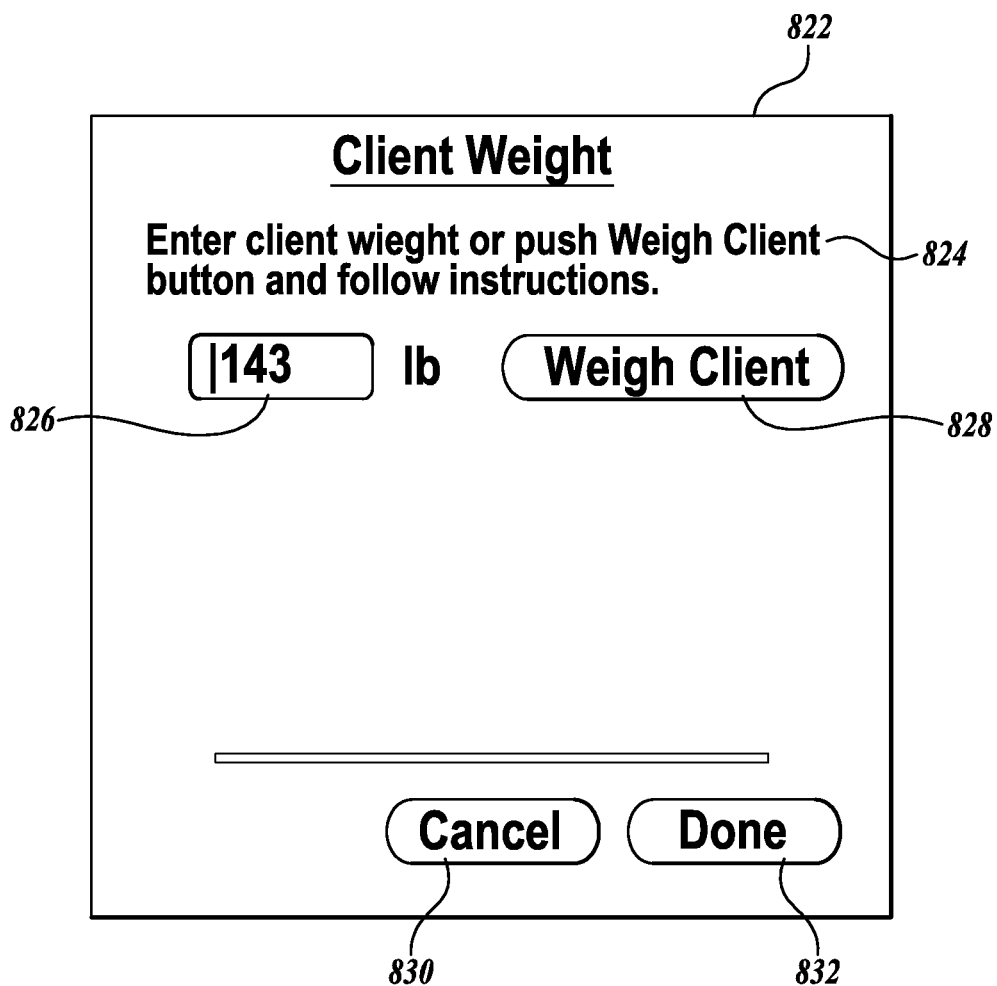
FIG. 13 is a diagrammatical illustration of a graphical user interface.

FIG. 13 is an illustration of a graphical user interface 822 for entering the patient 326 weight for block 416 of method 400 in FIG. 7. The graphical user interface 822 includes a text box 824 for providing instructions on entering the weight of the patient 326. The graphical user interface 822 includes a text box 826 for manually entering the weight of the patient 326. The graphical user interface 822 includes a weigh patient button 828 for automatically entering the weight of the patient 326. Clicking on the weigh patient button 828 calls up the automatic patient weight input subroutine 500 (FIG. 10). The graphical user interface 822 has a cancel button 830 and a done button 832. Clicking on the cancel button 830 closes the graphical user interface 822 without entering or updating the patient 326 weight. Clicking on the done button 832 enters the patient 326 weight in the gait analysis application 366 and/or in the onboard memory 208 of the sensor 302 and may close the graphical user interface 822.

Figure 14:
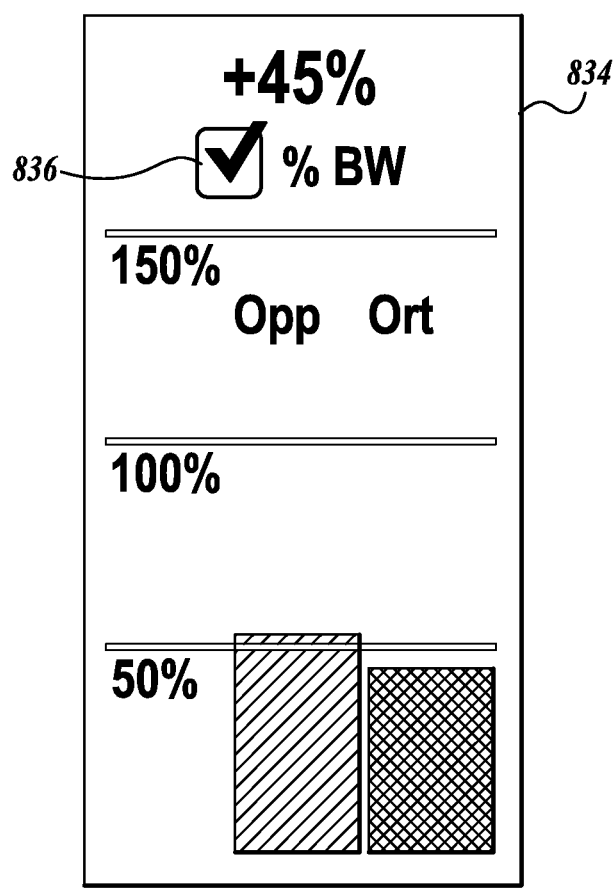
FIG. 14 is a diagrammatical illustration of a graphical user interface.

FIG. 14 is an illustration of a graphical user interface and bar graph 834 showing patient 326 weight information for block 420 of method 400 in FIGURE. The bar graph 834 graphs the percent of the patient 326 weight supported by the orthosis (Ort) and the opposite foot (Opp). The graphical user interface 834 includes a percent body weight (BW) checkbox 836. Clicking on the percent body weight checkbox 836 will show the information as a percentage of body weight. Specifically, FIG. 14 illustrates that the orthosis supports slightly less than 50% of the body weight of the patient 326 during walking, and the opposite foot supports slightly greater than 50% of the body weight of the patient 236.

Figure 15:
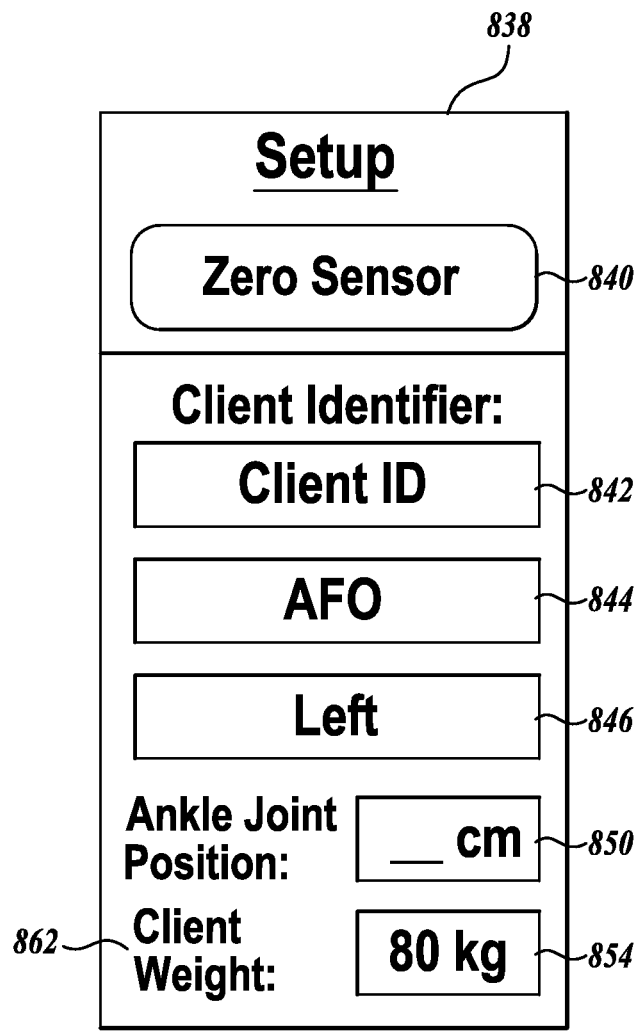
FIG. 15 is a diagrammatical illustration of a graphical user interface.

FIG. 15 is an illustration of a graphical user interface 838 for entering variables for block 424 of method 400 in FIG. 8. The graphical user interface 838 includes a button 840 for zeroing the sensor 302. The graphical user interface 838 includes a text box 842 for entering a client identifier. The graphical user interface 838 includes a text box 844 for entering the type of orthosis, such as FO, AFO, KAFO, or HKAFO. The graphical user interface 838 includes a text box 846 for entering whether the orthosis is for the left or the right leg. The graphical user interface 838 includes a label and text box 850 for entering the ankle joint position in centimeters measured from a reference point, such as the posterior of the heel along a horizontal line to the center of ankle joint rotation. The graphical user interface 838 includes a label 862 and text box 854 for manually entering or displaying the weight of the patient 326. The graphical user interface 838 may include anywhere on the interface, a text box for entering the shank angle.

Figure 16:
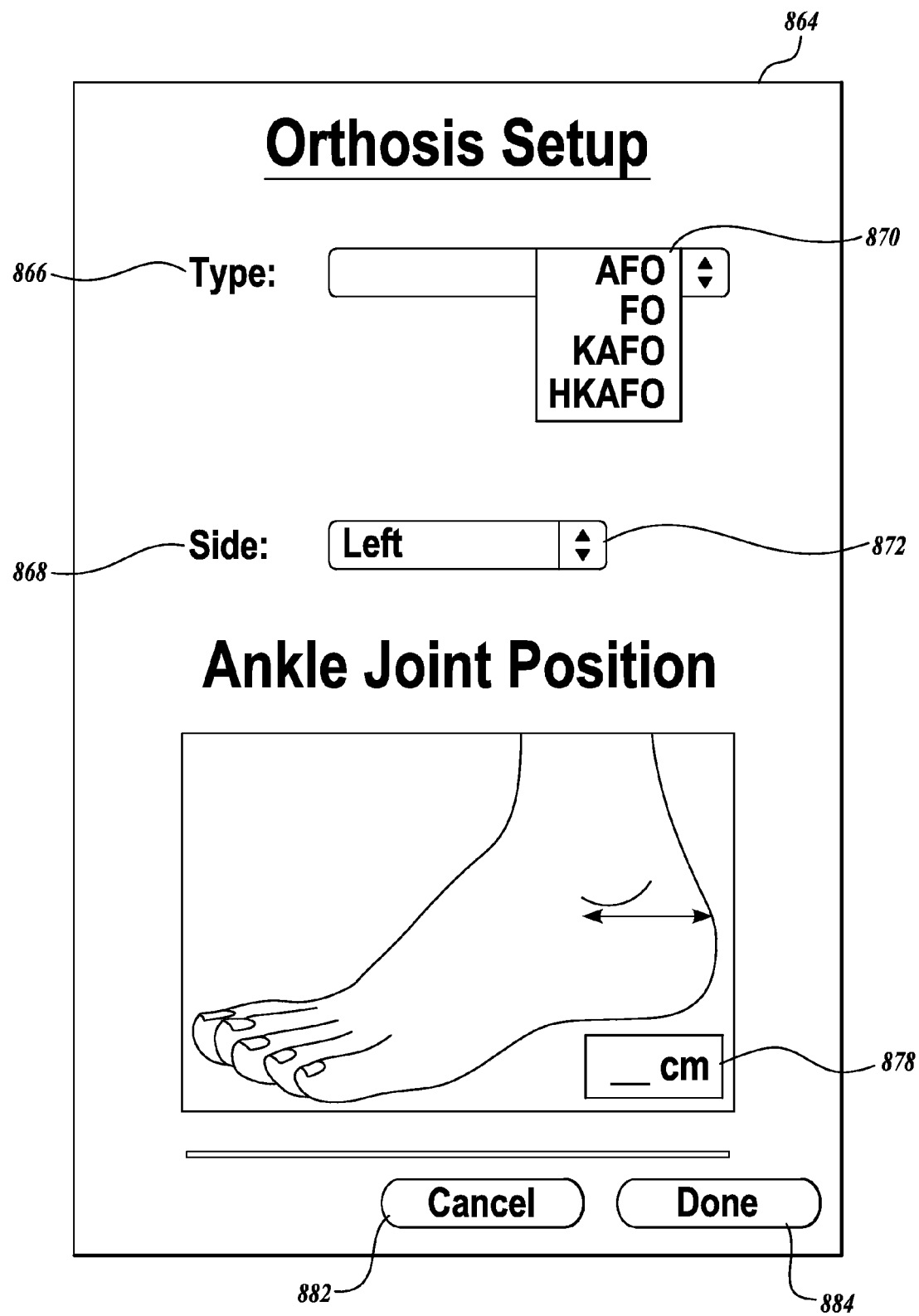
FIG. 16 is a diagrammatical illustration of a graphical user interface.

FIG. 16 is an illustration of another embodiment of a graphical user interface 864 for input entry for block 424 of method 400 in FIG. 8. The graphical user interface 864 includes a label 866 and dropdown menu 870 for selecting the type of the orthosis, such as AFO, FO, KAFO, and HKAFO. The graphical user interface 864 includes a label 868 and dropdown menu 872 for selecting either the left or the right side of the orthosis. The graphical user interface 864 includes a drawing and text box 878 for manually entering the distance of the ankle joint center of rotation from a reference point, such as the posterior of the heel along a horizontal line. The graphical user interface 864 may include anywhere on the interface, a text box for entering the shank angle. The graphical user interface 864 includes a cancel button 882 and a done button 884. Clicking on the cancel button 882 closes the graphical user interface 822 without entering the setup information. Clicking on the done button 832 enters the setup information in the gait analysis application 366 and/or in the onboard memory 208 of the sensor 302 and may close the graphical user interface 864.

Figure 17:
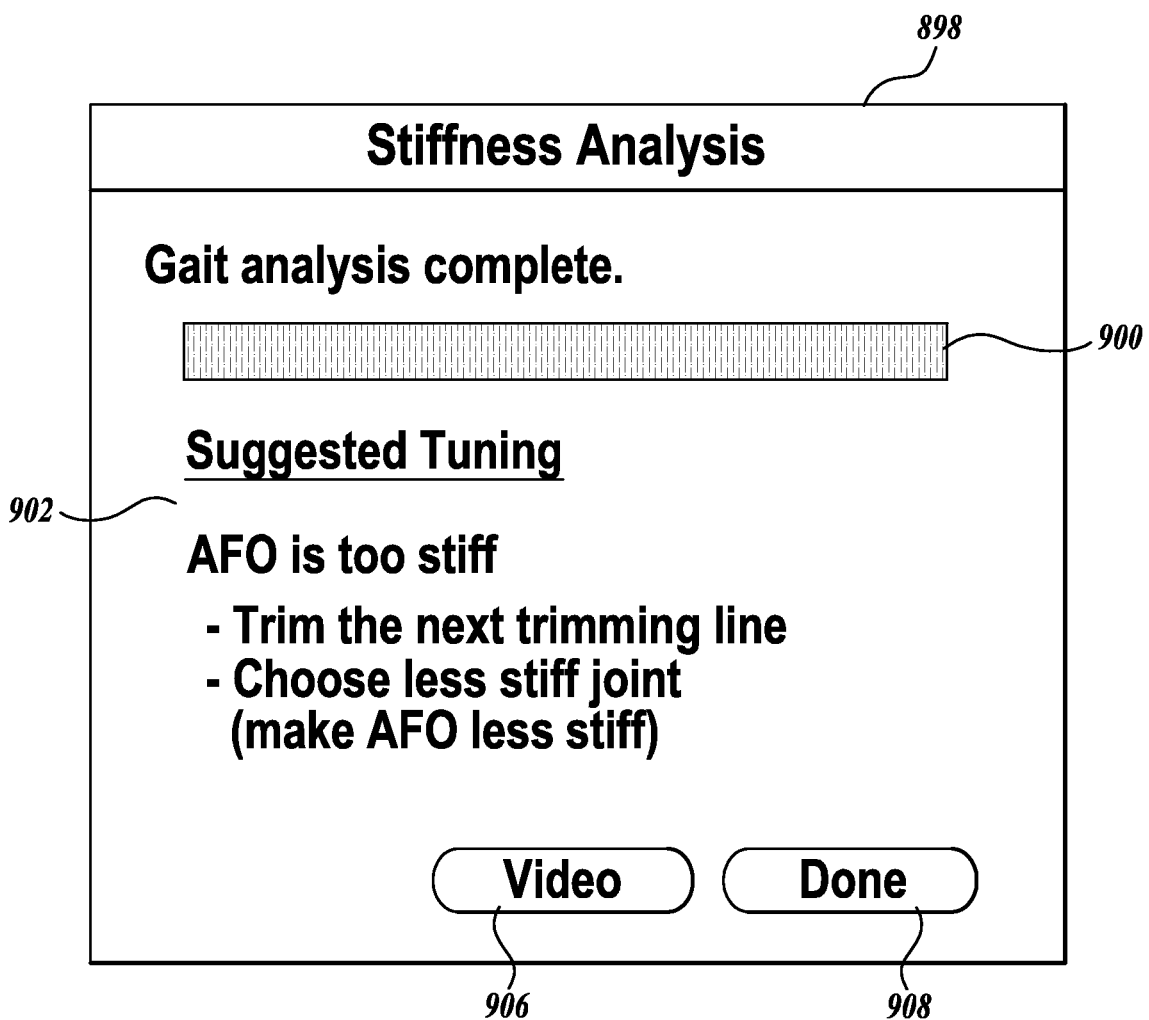
FIG. 17 is a diagrammatical illustration of a graphical user interface.
Figure 18:
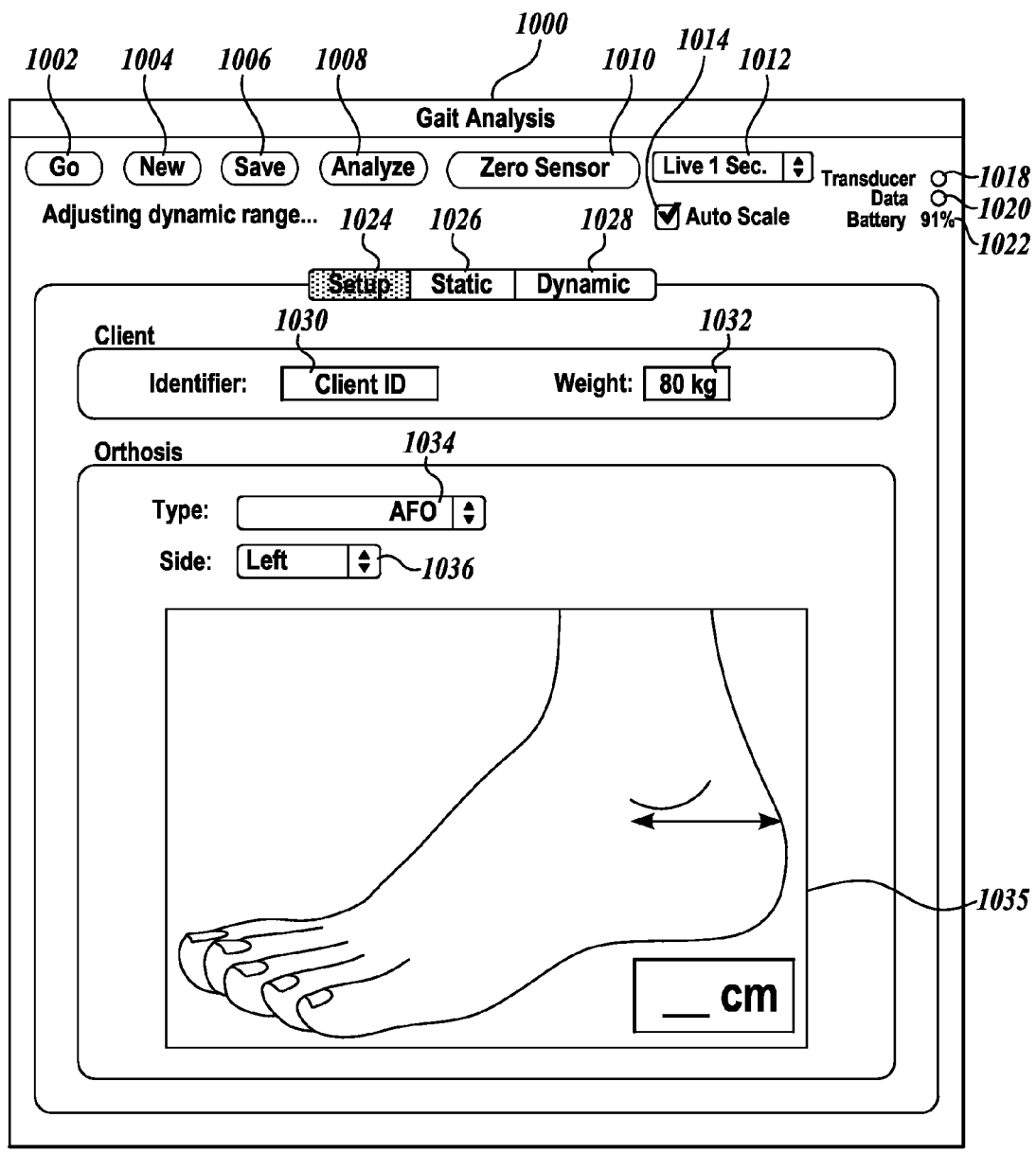
FIG. 18 is a diagrammatical illustration of a graphical user interface.

FIG. 17 is an illustration of a graphical user interface 898 for block 456 of the method 400 of FIG. 9. The graphical user interface 898 includes a progress bar 900 for indicating the progress of the analysis. When the analysis is complete, the progress bar 900 is full. The graphical user interface 898 includes a first label 902 for recommending tuning of the orthosis. The recommendations are provided by the graphical user interface 898 below the label 902. The recommendations may include whether the orthosis is stiffer than the optimal stiffness, and may recommend corrective action. The recommendations may include whether the orthosis shank angle is too large or too small and suggest the correct shank angle and may also display the angle visually. The graphical user interface 898 includes a video button 906 and a done button 908. Clicking on the video button 906 brings up a video of the patient 326 walking with the orthosis. Clicking on the done button 908 may close the graphical user interface 898.

FIG. 18 is an illustration of a graphical user interface 1000 for the gait analysis application 366 depicting three modes of operation. The modes include the setup 1024 mode, static 1026 mode, and dynamic 1028 mode. FIG. 18 is in the setup mode 1024. The graphical user interface 1000 includes a "go" button 1002, a "new" button 1004, an "analyze" button 1008, and a "zero sensor" button 1010. In the setup mode 1024, the go button 1002, new button 1004, save button 1006, analyze button 1008, and zero sensor button 1010 are inactive. The graphical user interface 1000 presents to the user 324, a drop down menu 1012 for selecting the rate of updating the data. The graphical user interface 1000 includes a label and check box 1014 for auto scaling. Checking the check box 1014 causes the graphs showing the data in real time to provide a suitable range. The graphical user interface 1000 includes a label and text box 1030 for entering the client ID. The graphical user interface 1000 includes a label and text box 1032 for manually entering the weight of the patient 326. The graphical user interface 1000 includes a label and drop down menu 1034 for entering the type of orthosis. For example, the user 324 may select from the dropdown menu 1034, FO, AFO, KAFO, or HKAFO. The graphical user interface 1000 includes a label and dropdown menu 1036 for entering whether the orthosis is a left or right orthosis. The graphical user interface 1000 includes a status indicator 1016 to monitor the status of the sensor 1018, and a status indicator 1020 to monitor whether data is streaming. The graphical user interface 1000 also monitors the battery condition with the battery condition status bar 1022. In the setup mode 1024, the sensor 302 is in a ready mode; and data streaming is not occurring. The graphical user interface 864 includes a drawing and text box 1035 for manually entering the distance of the ankle joint position relative to a reference point, such as the posterior of the heel along a horizontal line. The drawing shows how to measure the distance.

Figure 19:
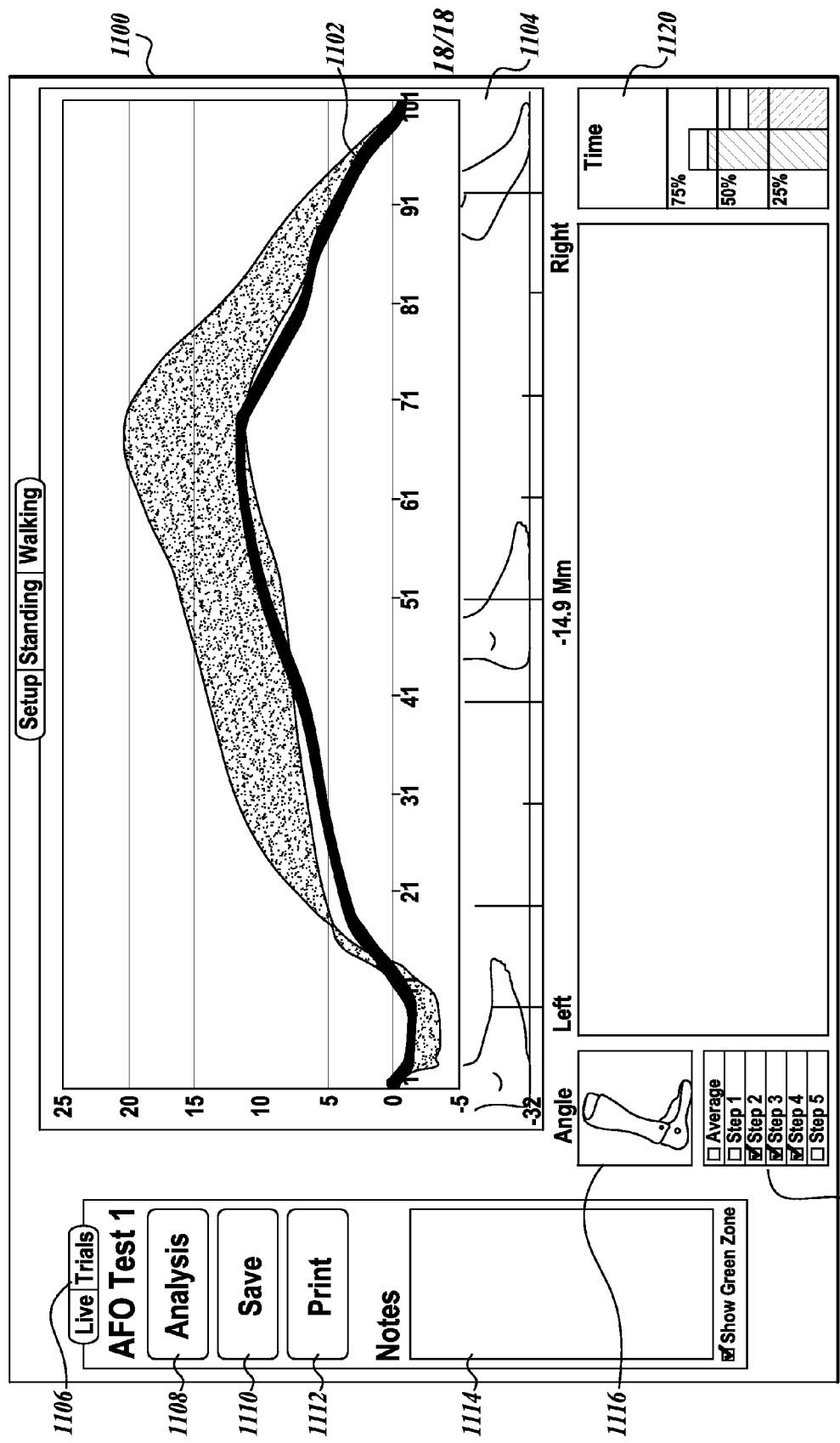
FIG. 19 is a diagrammatical illustration of a graphical user interface.

FIG. 19 is an illustration of a graphical user interface 1100, including a graph of the anterior/posterior moment plotted for a stance phase that may be displayed in block 414 of method 400 in FIG. 7. The moment curve 1102 has an initial relatively small negative moment, followed by a rapid increase in moment at a point about half-way to the mid-stance and continuing past the mid-stance to reach a maximum at a point about half-way from mid-stance to toe-off, and followed by a rapid decline thereafter to toe-off. The graphical user interface includes a visual display of the position of the foot corresponding to the curve 1102. The graphical user interface 1100 may include numerical values of the moment. The graphical user interface 1100 may include selection buttons 1106 labeled "live" and "trials" to allow the user 324 to select whether to view the patient walking in real time, or to recall previous trials. The graphical user interface 1100 may include an analysis button 1108, a save button 1110, and a print button 1112. Selecting the analysis button 1108 calls up the gait analysis application 366 to analyze the current moment data shown on the display. Selecting the save button 1110 saves the current moment data and current information. Selecting the print button 1112 prints the results. The graphical user interface 1100 may include a notes area 1114 for any text entries the user 324 desires to make. The graphical user interface 1100 may include a display 1116 showing the shank angle of the orthosis, which corresponds to the data shown on the display. The graphical user interface 1100 may include a listing 1118 of all the steps in a single continuous walking session. If a different step is selected, the graph and shank angle may change to match the step that is selected. The graphical user interface 1100 may include a bar graph 1120 of the percent. In some embodiments, both curves for the patient information and the model information can be plotted on the same graph. In some embodiments, a plurality of curves (or a shaded area) representing a plurality of stance phases may be plotted along with the model information. This provides a visual representation to the user 324 how far the orthosis stiffness and/or shank angle is from the model.

While illustrative embodiments have been illustrated and described, it will be appreciated that various changes can be made therein without departing from the spirit and scope of the invention.

The invention claimed is:

1. A method for tuning an orthosis, comprising:
via one or more computers, receiving patient information including moment forces experienced by a joint of a patient wearing an orthosis, wherein the orthosis has a degree of stiffness and/or shank angle; via one or more computers, comparing the patient information to model information, wherein the model information includes the moment forces of a correctly functioning joint; and changing the degree of stiffness and/or shank angle of the orthosis, wherein changing the degree of stiffness and/or shank angle includes a step selected from a group consisting of trimming a portion of the orthosis to decrease stiffness, and increasing or decreasing friction of a mechanical pivot linking two components of the orthosis.

2. The method of claim 1, further comprising, via the one or more computers, providing a deviation between the patient information and the model information.

3. The method of claim 1, further comprising, via the one or more computers, providing a recommendation on whether to increase or decrease stiffness and/or shank angle of the orthosis.

4. The method of claim 3, wherein the recommendation is sent over a network.

5. The method of claim 4, wherein the patient information is sent from a local computer over a network to a remote server, and the recommendation is sent from the remote server to the local computer.

6. The method of claim 1, wherein the joint is an ankle.

7. The method of claim 1, wherein the joint is a knee.

8. The method of claim 1, wherein the joint is a hip.

9. The method of claim 1, further comprising, via the one or more computers, receiving patient physical information that describes a distance from the joint to a reference point.

10. The method of claim 9, wherein the joint is an ankle, and the reference point is located at the posterior of the heel along a horizontal line from the ankle.

11. The method of claim 1, further comprising sending patient information over a network.

12. The method of claim 1, further comprising increasing or decreasing the shank angle of the orthosis.

13. The method of claim 1, wherein the patient information is compiled from information gathered during walking as a patient's foot contacts the ground.

14. The method of claim 1, wherein the model information is corrected for the weight of the patient.

15. The method of claim 1, wherein the model information is compiled from samples of correctly functioning joints.

16. The method of claim 1, further comprising displaying a graph of the patient information.

17. The method of claim 1, further comprising displaying a graph of the model information.

* * * * *